(12) United States Patent
Ke et al.

(10) Patent No.: US 8,088,375 B2
(45) Date of Patent: Jan. 3, 2012

(54) ANTI-VEGF ANTIBODY

(75) Inventors: Yaohuang Ke, San Francisco, CA (US); Weimin Zhu, San Francisco, CA (US); Guo-Liang Yu, Hillsborough, CA (US)

(73) Assignee: Epitomics, Inc., Burlingame, CA (US)

( * ) Notice: Subject to any disclaimer, the term of this patent is extended or adjusted under 35 U.S.C. 154(b) by 0 days.

(21) Appl. No.: 12/847,757

(22) Filed: Jul. 30, 2010

(65) Prior Publication Data

US 2011/0008367 A1 Jan. 13, 2011

Related U.S. Application Data

(62) Division of application No. 12/247,933, filed on Oct. 8, 2008, now Pat. No. 7,803,371.

(60) Provisional application No. 61/039,719, filed on Mar. 26, 2008.

(51) Int. Cl.
| | |
|---|---|
| *A61K 39/395* | (2006.01) |
| *A61K 39/00* | (2006.01) |
| *G01N 33/53* | (2006.01) |
| *G01N 33/536* | (2006.01) |
| *G01N 33/574* | (2006.01) |
| *C07K 16/00* | (2006.01) |
| *C07K 16/22* | (2006.01) |
| *C12P 21/08* | (2006.01) |

(52) U.S. Cl. .............. 424/130.1; 424/133.1; 424/141.1; 424/142.1; 424/145.1; 435/7.1; 435/7.21; 435/7.93; 530/387.1; 530/387.3; 530/388.1; 530/388.15; 530/388.23

(58) Field of Classification Search .................. None
See application file for complete search history.

(56) References Cited

U.S. PATENT DOCUMENTS

| | | | |
|---|---|---|---|
| 7,431,927 B2 | 10/2008 | Couto et al. | |
| 7,462,697 B2 | 12/2008 | Couto et al. | |
| 2004/0185040 A1 | 9/2004 | Garcia-Martinez et al. | |
| 2006/0216293 A1 | 9/2006 | Couto et al. | |

OTHER PUBLICATIONS

Rudikoff et al, Proc. Natl. Acad. Sci. USA vol. 79 p. 1979-1980, 1982.*
Barrios et al, J Molecular Recognition 17: 332-338, 2004.*
Piatesi et al, ChemBio Chem 5: 460-466, 2004.*
Wu et al, J. Mol. Biol. 294: 151-162, 1999.*
Stancovski et al, Proceedings of the National Academy of Science USA 88: 8691-8695, 1991.*
Riemer et al, Mol. Immunol. 42: 1121-1124, 2005.*
Popkov, M., et al. Human/mouse cross-reactive anti-VEGF receptor 2 recombiant antibodies selected from an immune b9 allotype rabbit antibody library. Journal of Immunological Methods. 2004, vol. 288, pp. 149-164.
Shiraishi, S., et al. lmmunohistochemical localization of vascular endothelial growth factor in the human placenta. Placenta. 1996, vol. 17, pp. 111-121.
Muller, Y., et al. VEGF and the Fab fragment of a humanized neutralizing antibody: crystal structure of the complex at 2.4 A resolution and mutational analysis of the interface. Structure. 1998, vol. 6, No. 9, pp. 1153-1167.
Rudikoff et al., Single amino acid substitution altering antigen-binding specificity. Proc Nat'l Aced Sci USA, vol. 79 (6); 1979-1983, Mar. 1982.
Barrios et al., Length of the antibody heavy chain complementarity determining region 3 as a specificity-determining factor. J. Molecular Recognition 17(4):332-338, Jul.-Aug. 2004.
Petrukhin et al., New therapeutic targets in atrophic age-related macular degeneration; Expert Opin Ther Targets. 11(5): 625-639, May 2007.
Yu et al., Interaction between bevacizumab and murine VEGF-A: a reassessment. Invest Ophthalmol Vis Sci, 49(2); 522-527, Feb. 2008.
Culy, "Bevacizumab: antiangiogenic cancer therapy", Drugs Today (Barc), 2005, 41:23-36 (abstract only).
Kerbel, et al., "A model of human cancer metastasis: extensive spontaneous and artificial metastasis of a human pigmented melanoma and derived variant sublines in nude mice", J Natl Cancer Inst., 1984, 72:93-108 (abstract only).
Lee, et al., "Immuno-PET of human colon xenograft- bearing BALB/c nude mice using 124I-CDR-grafted humanized A33 monoclonal antibody", J Nucl Med, 2001, 42:764-9.
List, "Vascular endothelial growth factor signaling pathway as an emerging target in hematologic malignancies", Oncologist, 2001, 6 Suppl, 5:24-31.
Mordenti, "Efficacy and concentration-response of murine anti-VEGF monoclonal antibody in tumor-bearing mice and extrapolation to humans", Toxicol Pathol, 1999, 27:14-21.
Presta, et al., "Humanization of an anti-vascular endothelial growth factor monoclonal antibody for the therapy of solid tumors and other disorders", Cancer Res, 1997, 15:4593-9.
Yu, et al., "A humanized anti-VEGF rabbit monoclonal antibody inhibits angiogenesis and blocks tumor growth in xenograft models", PLoS One, 2010, 5:e9072, 12pgs.

* cited by examiner

*Primary Examiner* — Phuong Huynh
(74) *Attorney, Agent, or Firm* — James S. Keddie; Bozicevic, Field & Francis LLP

(57) ABSTRACT

An antibody is provided. In certain cases, the antibody comprises: a) a heavy chain variable domain that comprises CDR regions that are substantially identical to the heavy chain CDR regions of a selected antibody and b) a light chain variable domain that comprises CDR regions that are substantially identical to the light chain CDR regions of the selected antibody, where the antibody binds a selected target.

19 Claims, 2 Drawing Sheets

FIG. 1 (page 1 of 2)

FIG. 1 (page 2 of 2)

US 8,088,375 B2

ANTI-VEGF ANTIBODY

CROSS-REFERENCING

This application is a divisional of U.S. patent application Ser. No. 12/247,933, filed on Oct. 8, 2008, and now U.S. Pat. No. 7,803,371, which application claims the benefit of U.S. provisional application Ser. No. 61/039,719, filed on Mar. 26, 2008.

BACKGROUND

Antibodies are proteins that bind a specific antigen. Generally, antibodies are specific for their targets, have the ability to mediate immune effector mechanisms, and have a long half-life in serum. Such properties make antibodies powerful therapeutics. Monoclonal antibodies are used therapeutically for the treatment of a variety of conditions including cancer, inflammation, and cardiovascular disease. There are currently over ten therapeutic antibody products on the market and hundreds in development.

There is a constant need for new antibodies.

SUMMARY OF THE INVENTION

An antibody is provided. In certain cases, the antibody comprises: a) a heavy chain variable domain that comprises CDR regions that are substantially identical to the heavy chain CDR regions of a selected antibody shown in FIG. 1 and b) a light chain variable domain that comprises CDR regions that are substantially identical to the light chain CDR regions of the selected antibody, where the antibody binds a selected target. In particular embodiments, the CDR regions of the antibody may collectively contain, for example, one, two, three, four, five or up to 10 amino acid differences (e.g., amino acid substitutions, deletions or insertions) relative to the CDR regions of the selected antibody. In certain cases, the CDR regions of a subject antibody may have an amino acid sequence that is defined by a consensus sequence derived from analysis of several related antibodies. In some embodiments the CDR regions of the antibody may be identical to the CDR regions of the selected antibody.

In particular embodiments, the antibody may comprise: a variable domain comprising: a) a heavy chain variable domain comprising: i. a CDR1 region that is identical in amino acid sequence to the heavy chain CDR1 region of a selected antibody of FIG. 1; ii. a CDR2 region that is identical in amino acid sequence to the heavy chain CDR2 region of the selected antibody; and iii. a CDR3 region that is identical in amino acid sequence to the heavy chain CDR3 region of the selected antibody; and b) a light chain variable domain comprising: i. a CDR1 region that is identical in amino acid sequence to the light chain CDR1 region of the selected antibody; ii. a CDR2 region that is identical in amino acid sequence to the light chain CDR2 region of the selected antibody; and iii. a CDR3 region that is identical in amino acid sequence to the light chain CDR3 region of the selected antibody; wherein the antibody specifically binds a selected target.

In certain embodiments, an antibody comprising: a) a variable domain comprising: i. a CDR1 region that is identical in amino acid sequence to the heavy chain CDR1 region of a selected antibody of FIG. 1; ii. a CDR2 region that is identical in amino acid sequence to the heavy chain CDR2 region of the selected antibody; and iii. a CDR3 region that is identical in amino acid sequence to the heavy chain CDR3 region of the selected antibody; and b) a light chain variable domain comprising: i. a CDR1 region that is identical in amino acid sequence to the light chain CDR1 region of the selected antibody; ii. a CDR2 region that is identical in amino acid sequence to the light chain CDR2 region of the selected antibody; and iii. a CDR3 region that is identical in amino acid sequence to the light chain CDR3 region of the selected antibody; or b) a variant of the variable domain of part a) that is otherwise identical to the variable domain of part a) except for a number of (e.g., 1, 2, 3, 4, 5, 6, 7 or 8) amino acid substitutions in the CDR regions, where the antibody binds a selected target and, in certain embodiments, the activity of the selected target.

In certain embodiments, the antibody may comprise the CDRs of a CDR consensus group selected from Table 1. In particular embodiments, the antibody may comprise: a) a heavy chain variable domain comprising: i. a CDR1 region comprising the CDR1 amino acid sequence of a CDR consensus group selected from Table 1; ii. a CDR2 region comprising the CDR2 amino acid sequence of the selected CDR consensus sequence; and iii a CDR3 region comprising the CDR3 amino acid sequence of the selected CDR consensus sequence; and b) a light chain variable domain comprising: i. a CDR1 region comprising the CDR1 amino acid sequence of the selected CDR consensus sequence; ii. a CDR2 region comprising the CDR2 amino acid sequence of the selected CDR consensus sequence; and iii a CDR3 region comprising the CDR3 amino acid sequence of the selected CDR consensus sequence; wherein said antibody specifically binds a selected target and, in certain embodiments, the activity of the selected target.

A pharmaceutical composition comprising a subject antibody and a pharmaceutically acceptable carrier is also provided.

A method is also provided. In certain embodiments, the method may comprise contacting a subject antibody with a target of the antibody under conditions suitable for binding of the antibody to the target to produce a complex.

Also provided is a method of blocking binding of a ligand to its receptor. In certain embodiments, this method may comprise: administering a subject antibody to a subject, wherein said antibody binds to either the receptor or the ligand in said subject and blocks binding of said ligand and its receptor.

The selected target may be VEGF.

BRIEF DESCRIPTION OF THE DRAWINGS

Figure 1:
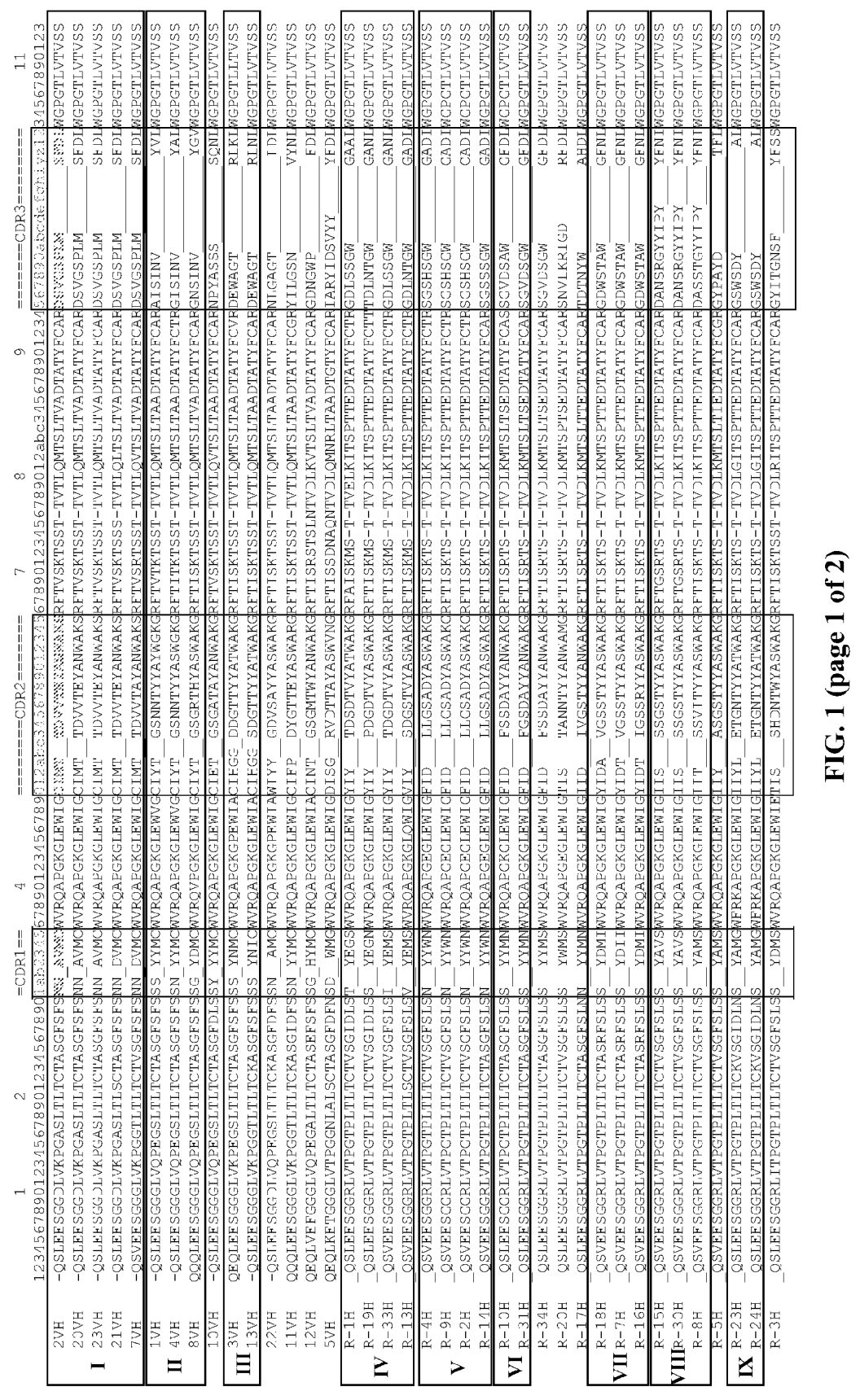
Figure 1:
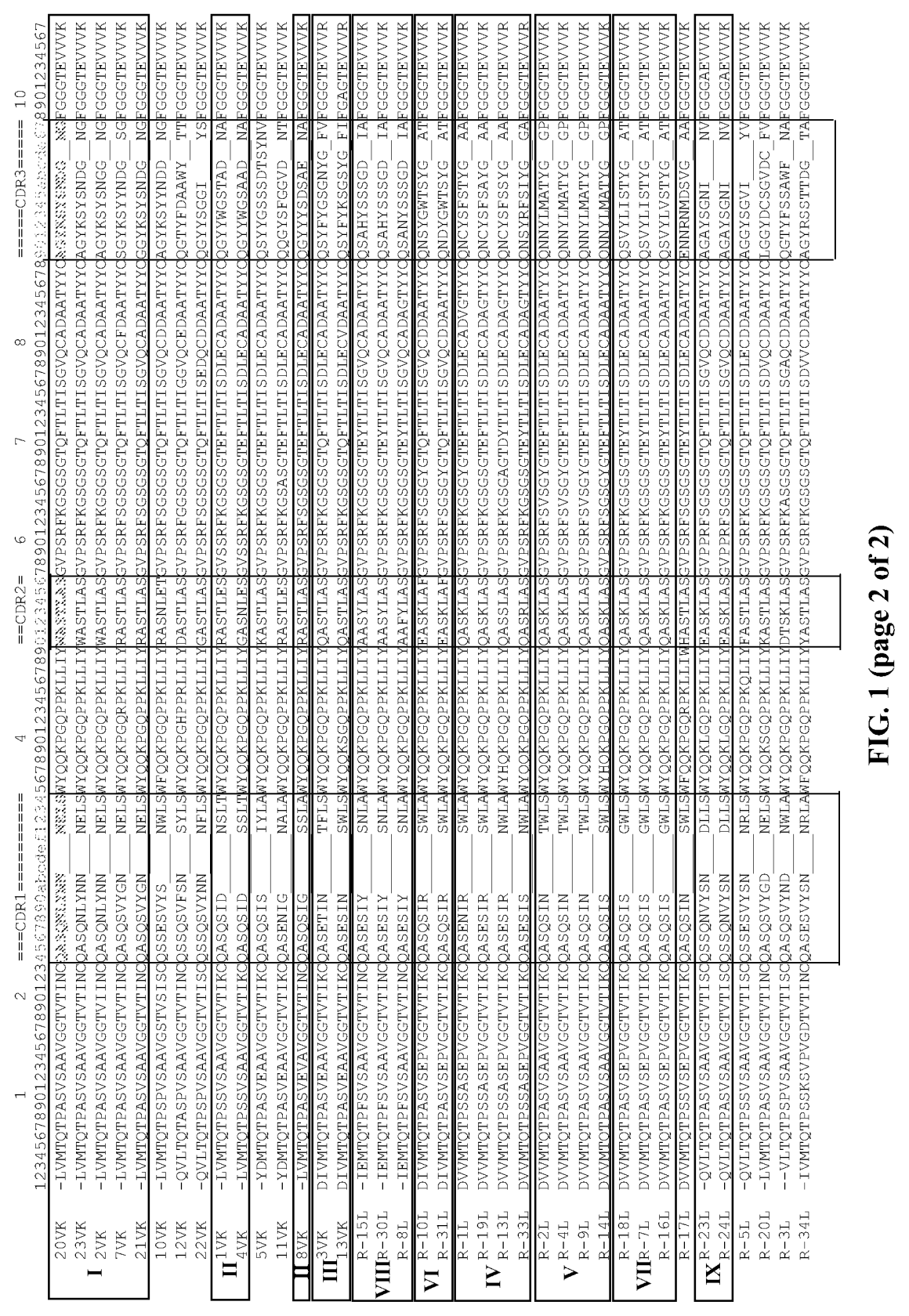

FIG. 1 shows the amino acid sequences of selected VEGF-blocking antibodies. Page 1 of FIG. 1 shows amino acid sequences of the heavy chains. Page 2 of FIG. 1 shows amino acid sequences of the corresponding light chains. The amino acid sequences of the CDRs of each antibody are boxed. The amino acid sequences shown in FIG. 1 are of antibodies that specifically bind to VEGF and neutralize VEGF activity. From top to bottom, FIG. 1 (page 1 of 2) SEQ ID NO: 1-38 and FIG. 1 (page 2 of 2) SEQ ID NO: 39-76.

DEFINITIONS

Before the present subject invention is described further, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an antibody" includes a plurality of such antibodies and reference to "a framework region" includes reference to one or more framework regions and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The terms "antibody" and "immunoglobulin" are used interchangeably herein. These terms are well understood by those in the field, and refer to a protein consisting of one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions.

The recognized immunoglobulin polypeptides include the kappa and lambda light chains and the alpha, gamma ($IgG_1$, $IgG_2$, $IgG_3$, $IgG_4$), delta, epsilon and mu heavy chains or equivalents in other species. Full-length immunoglobulin "light chains" (of about 25 kDa or about 214 amino acids) comprise a variable region of about 110 amino acids at the $NH_2$-terminus and a kappa or lambda constant region at the COOH-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the term are Fab', Fv, F(ab')$_2$, and or other antibody fragments that retain specific binding to antigen, and monoclonal antibodies. An antibody may be monovalent or bivalent.

Antibodies may exist in a variety of other forms including, for example, Fv, Fab, and (Fab')$_2$, as well as bi-functional (i.e. bi-specific) hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879-5883 (1988) and Bird et al., Science, 242, 423-426 (1988), which are incorporated herein by reference). (See, generally, Hood et al., "Immunology", Benjamin, N.Y., 2nd ed. (1984), and Hunkapiller and Hood, Nature, 323, 15-16 (1986)).

An immunoglobulin light or heavy chain variable region consists of a "framework" region (FR) interrupted by three hypervariable regions, also called "complementarity determining regions" or "CDRs". The extent of the framework region and CDRs have been precisely defined (see, "Sequences of Proteins of Immunological Interest," E. Kabat et al., U.S. Department of Health and Human Services, (1991)). The numbering of all antibody amino acid sequences discussed herein conforms to the Kabat system. The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen.

Chimeric antibodies are antibodies whose light and heavy chain genes have been constructed, typically by genetic engineering, from antibody variable and constant region genes belonging to different species. For example, the variable segments of the genes from a non-human monoclonal antibody may be joined to human constant segments, such as gamma 1 and gamma 3. An example of a therapeutic chimeric antibody is a hybrid protein composed of the variable or antigen-binding domain from a rabbit antibody and the constant or effector domain from a human antibody (e.g., the anti-Tac chimeric antibody made by the cells of A.T.C.C. deposit Accession No. CRL 9688), although other mammalian species may be used.

As used herein, the term "humanized antibody" or "humanized immunoglobulin" refers to an non-human (e.g., mouse or rabbit) antibody containing one or more amino acids that have been substituted with a correspondingly positioned amino acid from a human antibody. In some cases, humanized antibodies produce a reduced immune response in a human host, as compared to a non-humanized version of the same antibody.

It is understood that the humanized antibodies designed and produced by the present method may have amino acid substitutions which have substantially no effect on antigen binding or other antibody functions.

"Similar amino acids" defined as follows: gly, ala; val, ile, leu; asp, glu; asn, gln; ser, thr; lys, arg; and phe, tyr. In other words, gly and ala are similar amino acids; val, ile and leu are similar amino acids; asp and glu are similar amino acids; asn and gln are similar amino acids; ser and thr are similar amino acids; lys and arg are similar amino acids; and phe and tyr are similar amino acids. Substituting an amino acid for a similar amino acid is termed a "conservative amino acid substitution" herein. Amino acids that are not present in the same group as set forth above are "dis-similar" amino acids.

The term "specific binding" refers to the ability of an antibody to preferentially bind to a particular analyte that is present in a homogeneous mixture of different analytes. In certain embodiments, a specific binding interaction will discriminate between desirable and undesirable analytes in a sample, in some embodiments more than about 10 to 100-fold or more (e.g., more than about 1000- or 10,000-fold).

In certain embodiments, the affinity between an antibody and its target when they are specifically bound in a capture agent/analyte complex is characterized by a $K_D$ (dissociation constant) of less than $10^{-6}$ M, less than $10^{-7}$ M, less than $10^{-8}$ M, less than $10^{-9}$ M, less than $10^{-9}$ M, less than $10^{-11}$ M, or less than about $10^{-12}$ M or less.

A "variable region" of a heavy or light antibody chain is an N-terminal mature domain of the chains. All domains, CDRs and residue numbers are assigned on the basis of sequence alignments and structural knowledge. Identification and numbering of framework and CDR residues is as described in by Kabat, Chothia (Chothia, Structural determinants in the sequences of immunoglobulin variable domain. J Mol Biol 1998; 278:457-79) and others.

VH is the variable domain of an antibody heavy chain. VL is the variable domain of an antibody light chain, which could be of the kappa (K) or of the lambda isotype. K-1 antibodies have the kappa-1 isotype whereas K-2 antibodies have the kappa-2 isotype and Vλ is the variable lambda light chain.

As used herein, the terms "determining," "measuring," and "assessing," and "assaying" are used interchangeably and include both quantitative and qualitative determinations.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like. Polypeptides may be of any size, and the term "peptide" refers to polypeptides that are 8-50 residues (e.g., 8-20 residues) in length.

As used herein the term "isolated," when used in the context of an isolated antibody, refers to an antibody of interest that is at least 60% free, at least 75% free, at least 90% free, at least 95% free, at least 98% free, and even at least 99% free from other components with which the antibody is associated with prior to purification.

The terms "treatment" "treating" and the like are used herein to refer to any treatment of any disease or condition in a mammal, e.g. particularly a human or a mouse, and includes: a) preventing a disease, condition, or symptom of a disease or condition from occurring in a subject which may be predisposed to the disease but has not yet been diagnosed as having it; b) inhibiting a disease, condition, or symptom of a disease or condition, e.g., arresting its development and/or delaying its onset or manifestation in the patient; and/or c) relieving a disease, condition, or symptom of a disease or condition, e.g., causing regression of the condition or disease and/or its symptoms.

The terms "subject," "host," "patient," and "individual" are used interchangeably herein to refer to any mammalian subject for whom diagnosis or therapy is desired, particularly humans. Other subjects may include cattle, dogs, cats, guinea pigs, rabbits, rats, mice, horses, and so on.

"Corresponding amino acids", are amino acid residues that are at an identical position (i.e., they lie across from each other) when two or more amino acid sequences are aligned. Methods for aligning and numbering antibody sequences are set forth in great detail in Kabat supra, and others. As is known in the art (see, e.g. Kabat 1991 Sequences of Proteins of Immunological Interest, DHHS, Washington, D.C.), sometimes one, two or three gaps and/or insertions of up to one, two, three or four residues, or up to about 15 residues (particularly in the L3 and H3 CDRs) may be made to one or both of the amino acids of an antibody in order to accomplish an alignment.

A "natural" antibody is an antibody in which the heavy and light immunoglobulins of the antibody have been naturally selected by the immune system of a multi-cellular organism, as opposed to unnaturally paired antibodies made by e.g. phage display, or humanized antibodies. As such, certain antibodies do not contain any viral (e.g., bacteriophage M13)-derived sequences. Spleen, lymph nodes and bone marrow are examples of tissues that produce natural antibodies.

A "parent" antibody is an antibody is the target of amino acid substitutions. In certain embodiments, amino acids may be "donated" by a "donor" antibody to the parent antibody to produce an altered antibody.

"Related antibodies" are antibodies that have a similar sequence and produced by cells that have a common B cell ancestor. Such a B cell ancestor contains a genome having a rearranged light chain VJC region and a rearranged heavy chain VDJC region, and produces an antibody that has not yet undergone affinity maturation. "Naïve" or "virgin" B cells present in spleen tissue, are exemplary B cell common ancestors. Related antibodies bind to the same epitope of an antigen and are typically very similar in sequence, particularly in their L3 and H3 CDRs. Both the H3 and L3 CDRs of related antibodies have an identical length and a near identical sequence (e.g., differ by 0-4 residues). Related antibodies are related via a common antibody ancestor, the antibody produced in the naïve B cell ancestor. The term "related antibodies" is not intended to describe a group of antibodies that do not have a common antibody ancestor produced by a B-cell. In certain cases, related antibodies: i. bind to the same antigen; ii. each comprise heavy chain variable domains that have an overall amino acid sequence identity of at least 90% relative to one another; iii. each comprise light chain variable domains that have an overall amino acid sequence identity of at least 90% relative to one another; iv. have H3 CDRs that are identical in length and identical in sequence except for 0, 1 or 2 amino acid substitutions relative to one another; and v. have L3 CDRs that are identical in length and identical in sequence except for 0, 1 or 2 amino acid substitutions relative to one another;

A "blocking antibody", "neutralizing antibody" or "antibody that neutralizes" or any grammatical equivalent thereof refers to an antibody whose binding to a target results in inhibition binding to a target or of a biological activity of the target e.g., by at least about 20%, 30%, 40%, 50%, 80%, 95% or 99%. This inhibition of the biological activity of a target can be assessed by measuring one or more indicators of the target's biological activity, such as activation of a signal transduction pathway, binding, or cellular changes effected by the target. The biological activity of the targets described herein can be assessed by one or more of several standard in vitro or in vivo assays known in the art.

The term "VEGF" or its non-abbreviated form "vascular endothelial growth factor", as used herein, refers the protein products encoded by the VEGF gene. VEGF is involved in both vasculogenesis (the de novo formation of the embryonic circulatory system) and angiogenesis (the growth of blood vessels from pre-existing vasculature). All members of the VEGF family stimulate cellular responses by binding to tyrosine kinase receptors (the VEGFRs) on the cell surface, causing them to dimerize and become activated through transphosphorylation. The VEGF receptors have an extracellular portion containing 7 immunoglobulin-like domains, a single transmembrane spanning region and an intracellular portion containing a split tyrosine-kinase domain. VEGF-A binds to VEGFR-1 (Flt-1) and VEGFR-2 (KDR/Flk-1). VEGFR-2 appears to mediate almost all of the known cellular responses to VEGF. VEGF, its biological activities, and its receptors are well studied and are described in Matsumoto et al (VEGF receptor signal transduction Sci STKE. 2001:RE21 and Marti et al (Angiogenesis in ischemic disease. Thromb Haemost. 1999 Suppl 1:44-52). The term VEGF is intended to include recombinant VEGF molecules, which can be prepared by standard recombinant expression methods or purchased commercially (R & D Systems, Catalog No. 210-TA, Minneapolis, Minn.), as well as fusion proteins containing a VEGF molecule. Amino acid sequences of exemplary VEGFs that may be employed herein are found in the NCBI's Genbank database and a full description of human VEGF and its role in various diseases and conditions is found in NCBI's Online Mendelian Inheritance in Man database.

DETAILED DESCRIPTION

An antibody is provided. In certain cases, the antibody comprises: a) a heavy chain variable domain that comprises CDR regions that are substantially identical to the heavy chain CDR regions of a selected antibody shown in FIG. 1 and b) a light chain variable domain that comprises CDR regions that are substantially identical to the light chain CDR regions of the selected antibody, where the antibody binds a selected target. In particular embodiments, the CDR regions of the antibody may collectively contain, for example, one, two, three, four, five up to 10 amino acid differences (e.g., amino acid substitutions, deletions or insertions) relative to the CDR regions of the selected antibody. In some embodiments the CDR regions of the antibody may be identical to the CDR regions of the selected antibody. As would be readily apparent, such an antibody further contains framework sequences that position the CDRs.

In particular embodiments, a subject antibody may have: a) a heavy chain variable domain having an amino acid sequence that is at least 80% identical (e.g., at least 90%, at least 95% or at least 98% or 99% identical) to the heavy chain variable domain of a selected antibody shown in FIG. 1 and b) a light chain variable domain having an amino acid sequence that is at least 80% identical (e.g., at least 90%, at least 95% or at least 98% or 99% identical) to the light chain variable domain of the selected antibody.

In particular embodiments, the antibody may comprise: a) a heavy chain variable domain comprising: i. a CDR1 region that is identical in amino acid sequence to the heavy chain CDR1 region of a selected antibody of FIG. 1; ii. a CDR2 region that is identical in amino acid sequence to the heavy chain CDR2 region of the selected antibody; and iii. a CDR3 region that is identical in amino acid sequence to the heavy chain CDR3 region of the selected antibody; and b) a light chain variable domain comprising: i. a CDR1 region that is identical in amino acid sequence to the light chain CDR1 region of the selected antibody; ii. a CDR2 region that is identical in amino acid sequence to the light chain CDR2 region of the selected antibody; and iii. a CDR3 region that is identical in amino acid sequence to the light chain CDR3 region of the selected antibody; wherein the antibody specifically binds a selected target.

Immunization of a rabbit with a single antigen yields multiple antibodies that can be grouped by the relatedness of their sequence. The antibodies within each group are related to each other in that they are produced by cells that have a common naïve B cell ancestor. The antibody produced by the ancestral B cell does has not yet undergone affinity maturation, whereas the related antibodies have undergone affinity maturation and the final stage of B-cell development and have "evolved" from the common B-cell ancestor antibody in that they contain amino acid substitutions caused by somatic hypermutation, gene conversion and other cellular mutation events that occur during affinity maturation.

The amino acid sequence of related antibodies can be compared (e.g., by aligning those sequences), and the antibodies are classified according to their similarity to each other to identify related groups of antibodies. The antibodies of a group of related antibodies generally contain a near identical sequence, have CDR regions that are identical in length, and have differences in amino acid sequence in the framework and/or CDR regions. These differences indicate amino acids that can be substituted in either of the related antibodies. In certain cases, the amino acids at a position may be dis-similar amino acids, in which case an amino acid at that position may be substituted with any other amino acid, for example. In other cases, the amino acids at a position may be similar amino acids, in which case an amino acid at that position may be substituted with a similar amino acid, where a similar amino acid is defined above. In certain cases, the amino acid may be substituted from one related antibody to another, if the amino acid is different.

Since each of the CDRs of a particular consensus group were originally produced and effectively tested by the immune system of the immunized animal, substituting one amino acid for another consensus amino acid should be well tolerated by the antibody. The antibodies of FIG. 1 were aligned, groups of related antibodies were identified, and consensus sequences were identified. In certain cases, an antibody may comprise the CDRs of a CDR consensus group, where the CDR consensus groups are derived from sequence alignments of related antibodies. The consensus sequences of the antibodies of FIG. 1 are shown in Table 1. Table 1 indicates substitutable positions in a subject antibody, where a substitution may be to any other amino acid, a similar amino acid (i.e., a conservative amino acid substitution), or from one antibody to another, for example. Such methods are further described in U.S. patent application Ser. No. 10/984,473 (published as US-2006-0099204), which is incorporated by reference for disclosure of those methods.

In certain embodiments, the antibody may comprise the CDRs of a CDR consensus group selected from Table 1. In particular embodiments, the antibody may comprise: a) a heavy chain variable domain comprising: i. a CDR1 region comprising the CDR1 amino acid sequence of a CDR consensus group selected from Table 1; ii. a CDR2 region comprising the CDR2 amino acid sequence of the selected CDR consensus sequence; and iii a CDR3 region comprising the CDR3 amino acid sequence of the selected CDR consensus sequence; and b) a light chain variable domain comprising: i. a CDR1 region comprising the CDR1 amino acid sequence of the selected CDR consensus sequence; ii. a CDR2 region comprising the CDR2 amino acid sequence of the selected CDR consensus sequence; and iii a CDR3 region comprising the CDR3 amino acid sequence of the selected CDR consensus sequence; wherein said antibody specifically binds a selected target.

For example, such an antibody may comprise: a) a heavy chain variable domain having: i. a CDR1 of the formula: NNA/DVMC (SEQ ID NO:77), a CDR2 of the formula: CIMTTDVVTE/AYANWAKS (SEQ ID NO:78), and a CDR3 of the formula: DSVGSPLMSFDL (SEQ ID NO:79), and; b) a light chain variable domain having: a CDR1 of the formula: QASQN/SL/VYN/GNNELS (SEQ ID NO:80), a CDR2 of the formula: W/RASTLAS (SEQ ID NO:81) and a CDR3 of the formula: A/S/GGYKSYS/YND/GGN/SG (SEQ ID NO:82), where the antibody blocks VEGF.

TABLE 1

| CDR Consensus groups | Activity | Antibody | CDR 1 | SEQ ID NO. | CDR 2 | SEQ ID NO. | CDR 3 | SEQ ID NO. |
|---|---|---|---|---|---|---|---|---|
| HEAVY CHAIN | | | | | | | | |
| I | VEGF binding | 2, 7, 20, 21, 23 | NNA/DVMC | 77 | CIMTTDVVTE/AYANWAKS | 78 | DSVGSPLMSFDL | 79 |
| II | VEGF binding | 1, 4, 8 | SS/N/GYY/DMC | 83 | CIYTGSN/GN/RTY/HYAY/SWG/AKG | 84 | A/GI/NSINVYV/A/GL/V | 85 |
| III | VEGF binding | 3, 13 | SSYNM/IC | 89 | CIHGGD/SDGTTYYATWAKG | 90 | DEWAGTRLK/NL | 91 |
| IV | VEGF binding | R1, R19, R13, R33 | T/S/I/VYEG/MS/N | 95 | Y/VIYT/P/SDS/GD/STVYAT/SWAKG | 96 | G/TDLS/NS/TGWGAA/N/DL | 97 |
| V | VEGF binding | R2, R4, R9, R14 | NYYWN | 101 | FIDLLGSADYASWAKG | 102 | SGSH/SSGWG/CADI | 103 |
| VI | VEGF binding | R10, R31 | SYYMN | 107 | FID FS/GSDAYYANWAKG | 108 | SGVDSA/GWGFDL | 109 |
| VII | VEGF binding | R7, R16, R18 | SYDM/II | 113 | YIDA/TV/IGSST/RYYASWAKG | 114 | GDWSTAWGFNL | 115 |
| VIII | VEGF binding | R8, R15, R30 | SYAV/MS | 119 | IIS/TSSG/VS/ITYYASWAKG | 120 | DAN/SSR/TGYYIPYYFNI | 121 |
| IX | VEGF binding | R23, R24 | SYAMG | 125 | IIYLETGNTYYATWAKG | 126 | GSWSDYAL | 127 |
| LIGHT CHAIN | | | | | | | | |
| I | VEGF binding | 2, 7, 20, 21, 23 | QASQN/SL/VYN/GNNELS | 80 | W/RASTLAS | 81 | A/S/GGYKSYS/YND/GGN/SG | 82 |
| II | VEGF binding | 1, 4, 8 | QASQSID/GN/SSLT/A | 86 | R/GAST/NLE/AS | 87 | QGYYW/YG/SS/DT/A/SAD/ENA | 88 |
| III | VEGF binding | 3, 13 | QASET/SINT/SF/WLS | 92 | QASTLAS | 93 | QSYFYG/KSGN/SYGFV/I | 94 |
| IV | VEGF binding | R-1, R19, R13, R33 | QASEN/SIR/SS/NWLA | 98 | QASK/S/RLAS | 99 | QNC/SYS/RFST/A/S/IYGA/GA | 100 |
| V | VEGF binding | R2, R4, R9, R14 | QASQSIN/ST/SWLS | 104 | QASKLAS | 105 | QNNYLMATYGGP | 106 |
| VI | VEGF binding | R10, R31 | QASQSIRSWLA | 110 | EASKLAF | 111 | QNS/DYGWTSYGAT | 112 |
| VII | VEGF binding | R7, R16, R18 | QASQSISGWLS | 116 | QASKLAS | 117 | QSVYLI/VSTYGAT | 118 |
| VIII | VEGF binding | R8, R15, R30 | QASESIYSNLA | 122 | AAS/FYLAS | 123 | QSAH/NYSSSGDIA | 124 |
| IX | VEGF binding | R23, R24 | QSSQNVYSNDLLS | 128 | EASKLAS | 129 | AGAYSGNINV | 130 |

In a particular embodiment, the antibody may comprise: a) a heavy chain variable domain comprising CDRs comprising an amino acid sequence of the formulae: CDR1: (S/N)(N/S/-) YXM(C/N/S/I); CDR2: (C/F/Y/I)I(M/Y/D/S)(T/-)(G/-)XXXX(T/A)(Y/E/D/V) YA(N/S/T)WAK(G/S) (SEQ ID NO:131); CDR3: (G/D/S)(S/D/G/A)XXXX(L/W/Y/-)(X/-)(X/-) (X/-)(X/-)(Y/G/S/-)(F/A/Y/-)(A/N/D)(L/I), and; b) a light chain variable domain comprising CDRs comprising an amino acid sequence of the formulae: CDR1: Q(A/S)S(E/Q)(S/N)(L/V/I)X(S/N/G/-)(N/D/-)(N/T/S/D/G)XL(S/T/A); CRD2: XAS(T/K/Y)L(A/E)S (SEQ ID NO:132); CDR3: (A/Q)(G/N/S)X(Y/K)XXXX(X/-) (G/D/-)(X/-)(X/-)X(G/T/A/P/V), wherein X is any amino acid, – denotes no residue, / denotes alternative amino acid present at a position, and ( ) denotes one amino acid position. This antibody blocks VEGF.

Modified Antibodies

The above-described antibodies may modified by substituting, adding, or deleting at least one amino acid. In one embodiment, an above-described the amino acid sequence of a subject antibody is modified to provide a humanized antibody for human therapeutic use, or another type of modified antibody. In general, these modified antibodies have the general characteristics of the above-described rabbit antibodies and contain at least the CDRs of an above-described rabbit antibody, or, in certain embodiments, CDRs that are very similar to the CDRs of an above-described rabbit antibody.

Humanized Antibodies

In one embodiment, therefore, the invention provides humanized versions of the above-described antibodies. In general, humanized antibodies are made by substituting amino acids in the framework regions of a parent non-human antibody to produce a modified antibody that is less immunogenic in a human than the parent non-human antibody. Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332). In certain embodiments, framework substitutions are identified by modeling of the interactions of the CDR and framework residues to identify framework residues important for antigen binding and sequence comparison to identify unusual framework residues at particular positions (see, e.g., U.S. Pat. No. 5,585,089; Riechmann et al., Nature 332:323 (1988)). Additional methods for humanizing antibodies contemplated for use in the present invention are described in U.S. Pat. Nos. 5,750,078; 5,502,167; 5,705,154; 5,770,403; 5,698,417; 5,693,493; 5,558,864; 4,935,496; and 4,816,567, and PCT publications WO 98/45331 and WO 98/45332. In particular embodiments, a subject rabbit antibody may be humanized according to the methods set forth in published U.S. patent applications 20040086979 and 20050033031. Accordingly, the antibodies described above may be humanized using methods that are well known in the art.

In one embodiment of particular interest, a subject antibody may be humanized in accordance with the methods set forth in great detail in U.S. patent application Ser. No. 10/984,473, filed on Nov. 8, 2004 and entitled "Methods for antibody engineering", which application is incorporated by reference in its entirety. In general, this humanization method involves identifying a substitutable position of an antibody by comparing sequences of antibodies that bind to the same antigen, and replacing the amino acid at that position with a different amino acid that is present at the same position of a similar human antibody. In these methods, the amino acid sequence of a parental rabbit antibody is compared to (i.e., aligned with) the amino acid sequences of other related rabbit antibodies to identify variation tolerant positions. The amino acid sequence of the variable domain of the parental rabbit antibody is usually compared to a database of human antibody sequences, and a human antibody that has an amino acid sequence that is similar to that of the parental antibody is selected. The amino acid sequences of the parental antibody and the human antibody are compared (e.g., aligned), and amino acids at one or more of the variation tolerant positions of the parental antibody are substituted by correspondingly positioned amino acids in the human antibody. In this humanization method, the CDR regions of the antibody may be humanized in addition to the framework regions.

The above-discussed variation tolerant position substitution methods are readily incorporated into any known humanization method and are also readily employed to produce humanized antibodies containing CDR regions that are altered with respect to the CDR regions of the parent antibody. Accordingly humanized antibodies containing altered versions of the CDRs of the above-described antibodies are provided.

As noted above, the subject antibody may be modified to provide a modified antibody. In particular embodiments, this method include making one or more amino acid substitutions (e.g., one, up to two, up to three, up to four or up to five of more, usually up to 10 or more). An amino acid substitution may be at any position, and the amino acid at that position may be substituted by an amino acid of any identity. In certain embodiments, a modified antibody may have the same general characteristics of the above-described rabbit antibodies. In one embodiment, after a substitutable position has been identified using the methods of U.S. Ser. No. 10/984,473, the amino acids at that position may be substituted. In particular embodiments, an amino acid substitution may be a humanizing substitution (i.e., a substitution that make the amino acid sequence more similar to that of a human antibody), a directed substitution (e.g., a substitution that make the amino acid sequence of an antibody more similar to that of a related antibody in the same group), a random substitution (e.g., a substitution with any of the 20 naturally-occurring amino acids) or a conservative substitution (e.g., a substitution with an amino acid having biochemical properties similar to that being substituted).

In certain embodiments, modified antibodies of the invention may contain a heavy or light chain that is encoded by a polynucleotide that hybridizes under high stringency conditions to a rabbit heavy or light chain-encoding nucleic acid. High stringency conditions include incubation at 50° C. or higher in 0.1×SSC (15 mM saline/0.15 mM sodium citrate).

In certain embodiments, modified antibodies of the invention may contain a heavy or light chain that is encoded by a polynucleotide that is at least 80% identical to (e.g., at least 85%, at least 90%, at least 95%, at least 98%) a rabbit heavy or light chain-encoding nucleic acid. The percentage identity is based on the shorter of the sequences compared. Well known programs such as BLASTN (2.0.8) (Altschul et al. (1997) *Nucl. Acids. Res.* 25:3389-3402) using default parameters and no filter may be employed to make a sequence comparison.

Methods of Use

The above-described antibodies may be employed in a variety of methods. One such method comprises: contacting a subject antibody with a target of the antibody under conditions suitable for binding of the antibody to the target to produce a complex. Such a method may be performed by ELISA or western blotting, or by any one of many immunological detection methods known in the art, for example. In other embodiments, a method of blocking binding of a ligand to its receptor is provided. In these embodiments, the method comprises: administering a subject antibody to a subject, where the antibody binds to either the receptor or the ligand in said subject and blocks binding thereof.

A subject antibody inhibits at least one activity of its target in the range of about 20% to 100%, e.g., by at least about 10%, at least about 20%, at least about 30%, at least about 40%, at least about 50%, at least about 60%, usually up to about 70%, up to about 80%, up to about 90% or more. In certain assays, a subject antibody may inhibits its target with an $IC_{50}$ of $1 \times 10^{-7}$ M or less (e.g., $1 \times 10^{-7}$ M or less, $1 \times 10^{-8}$ M or less, $1 \times 10^{-9}$ M or less, usually to $1 \times 10^{-12}$ M or $1 \times 10^{-13}$ M). In assays in which a mouse is employed, a subject antibody may have an $ED_{50}$ of less then 1 µg/mouse (e.g., 10 ng/mouse to about 1 µg/mouse).

The protocols that may be employed in these methods are numerous, and include but are not limited to cell-free assays, e.g., binding assays; cellular assays in which a cellular phenotype is measured, e.g., gene expression assays; and in vivo assays that involve a particular animal (which, in certain embodiments may be an animal model for a condition related to the target). In certain cases, the assay may be a vascularization assay.

In certain embodiments, a subject antibody may be contacted with a cell in the presence of VEGF, and a VEGF response phenotype of the cell monitored.

Exemplary VEGF assays include assays using isolated protein in a cell free systems, in vitro using cultured cells or in vivo assays. Exemplary VEGF assays include, but are not limited to a receptor tyrosine kinase inhibition assay (see, e.g., Cancer Research Jun. 15, 2006; 66:6025-6032), an in vitro HUVEC proliferation assay (FASEB Journal 2006; 20: 2027-2035), an in vivo solid tumor disease assay (U.S. Pat. No. 6,811,779) and an in vivo angiogenesis assay (FASEB Journal 2006; 20: 2027-2035). These assays are well known in the art. The descriptions of these assays are hereby incorporated by reference.

Exemplary TNF-α assays include in vitro assays using cell free systems or using cultured cells or in vivo assays. As such, TNF-α assays include in vitro human whole blood assay and cell mediated cytotoxicity assay (U.S. Pat. No. 6,090,382), in vitro tumor human killing assay (see, e.g., published U.S. patent application 20040185047), in vivo tumor regression assay (USP Application 20040002589). Additional TNF-α assays are described in a variety of publications, including 20040151722, 20050037008, 20040185047, 20040138427, 20030187231, 20030199679, and Balazovich (Blood 1996 88: 690-696).

Methods for Producing Antibodies

In many embodiments, the nucleic acids encoding a subject monoclonal antibody are introduced directly into a host cell, and the cell incubated under conditions sufficient to induce expression of the encoded antibody. The antibodies of this invention are prepared using standard techniques well known to those of skill in the art in combination with the polypeptide and nucleic acid sequences provided herein. The polypeptide sequences may be used to determine appropriate nucleic acid sequences encoding the particular antibody disclosed thereby. The nucleic acid sequence may be optimized to reflect particular codon "preferences" for various expression systems according to standard methods well known to those of skill in the art.

Any cell suitable for expression of expression cassettes may be used as a host cell. For example, yeast, insect, plant, etc., cells. In many embodiments, a mammalian host cell line that does not ordinarily produce antibodies is used, examples of which are as follows: monkey kidney cells (COS cells), monkey kidney CVI cells transformed by SV40 (COS-7, ATCC CRL 165 1); human embryonic kidney cells (HEK-293, Graham et al. J. Gen Virol. 36:59 (1977)); baby hamster kidney cells (BHK, ATCC CCL 10); chinese hamster ovary-cells (CHO, Urlaub and Chasin, Proc. Natl. Acad. Sci. (USA) 77:4216, (1980); mouse sertoli cells (TM4, Mather, Biol. Reprod. 23:243-251 (1980)); monkey kidney cells (CVI ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (hep G2, HB 8065); mouse mammary tumor (MMT 060562, ATCC CCL 51); TRI cells (Mather et al., Annals N.Y. Acad. Sci 383:44-68 (1982)); NIH/3T3 cells (ATCC CRL-1658); and mouse L cells (ATCC CCL-1). Additional cell lines will become apparent to those of ordinary skill in the art. A wide variety of cell lines are available from the American Type Culture Collection, 10801 University Boulevard, Manassas, Va. 20110-2209.

Methods of introducing nucleic acids into cells are well known in the art. Suitable methods include electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995. In some embodiments lipofectamine and calcium mediated gene transfer technologies are used.

After the subject nucleic acids have been introduced into a cell, the cell is typically incubated, normally at 37° C., sometimes under selection, for a period of about 1-24 hours in order to allow for the expression of the antibody. In most embodiment, the antibody is typically secreted into the supernatant of the media in which the cell is growing in.

In mammalian host cells, a number of viral-based expression systems may be utilized to express a subject antibody. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355-359 (1984)). The efficiency of expression may be enhanced by the inclusion of appropriate transcription enhancer elements, transcription terminators, etc. (see Bittner et al., Methods in Enzymol. 153:51-544 (1987)).

For long-term, high-yield production of recombinant antibodies, stable expression may be used. For example, cell lines, which stably express the antibody molecule, may be engineered. Rather than using expression vectors which contain viral origins of replication, host cells can be transformed with immunoglobulin expression cassettes and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into a chromosome and grow to form foci which in turn can be cloned and expanded into cell lines. Such engineered cell lines may be particularly useful in screening and evaluation of compounds that interact directly or indirectly with the antibody molecule.

Once an antibody molecule of the invention has been produced, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In many embodiments, antibodies are secreted from the cell into culture medium and harvested from the culture medium.

Formulations and Administration

The antibodies of the invention may be administered in any manner which is medically acceptable. This may include injections, by parenteral routes such as intravenous, intravascular, intraarterial, subcutaneous, intramuscular, intratumor, intraperitoneal, intraventricular, intraepidural, or others as well as oral, nasal, ophthalmic, rectal, or topical. Sustained release administration is also specifically included in the invention, by such means as depot injections or erodible implants. Localized delivery is particularly contemplated, by such means as delivery via a catheter to one or more arteries, such as the renal artery or a vessel supplying a localized tumor.

The subject antibodies may be formulated with a pharmaceutically acceptable carrier. The term "pharmaceutically acceptable carrier" means one or more organic or inorganic ingredients, natural or synthetic, with which the antibody is combined to facilitate its application. A suitable carrier includes sterile saline although other aqueous and non-aqueous isotonic sterile solutions and sterile suspensions known to be pharmaceutically acceptable are known to those of ordinary skill in the art. An "effective amount" refers to that amount which is capable of ameliorating or delaying progression of the diseased, degenerative or damaged condition. An effective amount can be determined on an individual basis and will be based, in part, on consideration of the symptoms to be treated and results sought. An effective amount can be determined by one of ordinary skill in the art employing such factors and using no more than routine experimentation.

In one embodiment a subject antibody is administered to a patient by intravenous, intramuscular or subcutaneous injection. An antibody may be administered within a dose range between about 0.1 mg/kg to about 100 mg/kg; between about 1 mg/kg to 75 mg/kg; or about 10 mg/kg to 50 mg/kg. The antibody may be administered, for example, by bolus injunction or by slow infusion. Slow infusion over a period of 30 minutes to 2 hours may be used.

Utility

A subject antibody is useful for treating a disorder relating to its target.

In one embodiment, the invention provides a method of treating a subject for a VEGF-related condition. The method generally involves administering a subject antibody to a subject having a VEGF-related disorder in an amount effective to treat at least one symptom of the VEGF-related disorder. VEGF-related conditions are generally characterized by excessive vascular endothelial cell proliferation, vascular permeability, edema or inflammation such as brain edema associated with injury, stroke or tumor; edema associated with inflammatory disorders such as psoriasis or arthritis, including rheumatoid arthritis; asthma; generalized edema associated with burns; ascites and pleural effusion associated with tumors, inflammation or trauma; chronic airway inflammation; capillary leak syndrome; sepsis; kidney disease associated with increased leakage of protein; and eye disorders such as age related macular degeneration and diabetic retinopathy. Such conditions include breast, lung, colorectal and renal cancer.

Kits

Also provided by the subject invention are kits for practicing the subject methods, as described above. The subject kits at least include one or more of: a subject antibody, a nucleic acid encoding the same, or a cell containing the same. The subject antibody may be humanized. Other optional components of the kit include: buffers, etc., for administering the antibody or for performing an activity assay. The nucleic acids of the kit may also have restrictions sites, multiple cloning sites, primer sites, etc to facilitate their ligation to non-rabbit antibody nucleic acids. The various components of the kit may be present in separate containers or certain compatible components may be precombined into a single container, as desired.

In addition to above-mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Also provided by the subject invention are kits including at least a computer readable medium including programming as discussed above and instructions. The instructions may include installation or setup directions. The instructions may include directions for use of the invention with options or combinations of options as described above. In certain embodiments, the instructions include both types of information.

Providing the software and instructions as a kit may serve a number of purposes. The combination may be packaged and purchased as a means for producing rabbit antibodies that are less immunogenic in a non-rabbit host than a parent antibody, or nucleotide sequences thereof.

The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., CD-ROM, diskette, etc, including the same medium on which the program is presented.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

EXAMPLES

The antibody were obtained from rabbit hybridoma producing antibodies that block the interaction of VEGF with its receptor (VEGF-R2). The hybridoma were generated by fusing immunized rabbit splenocytes with the rabbit hybridoma fusion partner 240E-W2.

Rabbits were immunized with an Fc fusion protein. To express the fusion protein, the human VEGF165 coding sequence was cloned into the C-terminal of rabbit IgG Fc which contains the signal peptide sequence of rabbit IgG heavy chain at its N-terminus. The fusion protein was produced in HEK 293 cells and secreted into the culture medium. To obtain the pure protein for immunization, the supernatant was harvested and purified through a protein A column. The eluted protein was dialyzed against PBS buffer.

New Zealand white rabbits were immunized with the immunogen. Each rabbit received a primary immunization by subcutaneous injection of 0.4 mg of the purified protein with complete Freund's or TiterMax adjuvant. The animals were then boosted by subcutaneous injection of 0.2 mg of the protein with incomplete Freund's or TiterMax once every three weeks. The final boost (0.4 mg protein in saline) was given intravenously 4 days before splenectomy.

Cell fusions were performed following the conventional protocol of Spieker-Polet using PEG. The ratio of splenocytes to the fusion partner was 2:1. The fused cells were plated in 96-well plates and HAT was added after 48 hrs to select for hybridomas.

Direct ELISA was performed to identify antibodies that block binding of VEGF to a VEGF-R2 fusion protein coated onto a microtiter plate. Antibodies identified in this assay were then were screened for blocking VEGF interaction with its receptor in a ligand-receptor assay. The blocking antibodies were identified by their inhibition of binding of Fc-VEGF-R2 (Extracellular domain) or VEGF-Fc in solution to Fc-VEGF or Fc-VEGF-R2 coated on plates.

cDNAs coding the heavy and light chains of the antibodies were cloned and sequenced.

That which is claimed is:

1. A method of reducing binding of human VEGF to a human VEGFR2 (VEGF Receptor 2), comprising:
   contacting human VEGF with a monoclonal antibody that binds to said human VEGF and comprises:
   a) an antibody variable domain comprising:
      i. a heavy chain variable domain comprising a CDR1 region identical to amino acid residues 30-35 of SEQ ID NO: 4, a CDR2 region identical to amino acid residues 50-66 of SEQ ID NO: 4 and a CDR3 region identical to amino acid residues 98-109 of SEQ ID NO: 4; and
      ii. a light chain variable domain comprising a CDR1 region identical to amino acid residues 23-35 of SEQ ID NO: 43, a CDR2 region identical to amino acid residues 51-57 of SEQ ID NO: 43 and a CDR3 region identical to amino acid residues 90-101 of SEQ ID NO: 43; or
   b) a variant of said antibody variable domain that is otherwise identical to said antibody variable domain except for up to 8 amino acid substitutions in said CDR regions, wherein binding of the monoclonal antibody to said human VEGF reduces binding of said human VEGF to said VEGFR2 receptor.

2. The method of claim 1, wherein said VEGFR2 is present on a cell in vitro.

3. The method of claim 1, wherein said VEGFR2 is isolated.

4. The method of claim 1, wherein said VEGFR2 is present on a cell in vivo.

5. The method of claim 4, wherein said contacting is done by administering said monoclonal antibody to a human or mouse subject.

6. The method of claim 5, wherein said monoclonal antibody inhibits a VEGFR2-mediated activity of human VEGF in said subject.

7. The method of claim 5, wherein said subject has a VEGF-related condition.

8. The method of claim 5, wherein said monoclonal antibody is administered to said subject in a pharmaceutically-acceptable carrier.

9. The method of claim 1, wherein the amino acid sequences of the framework regions of the heavy chain and the light chain of said monoclonal antibody are different from the framework regions of SEQ ID NO: 4 and SEQ ID NO: 43, respectively, due to humanization of said monoclonal antibody.

10. The method of claim 1, wherein said monoclonal antibody comprises a human constant domain.

11. The method of claim 1, wherein said monoclonal antibody is a monovalent antibody.

12. The method of claim 1, wherein said monoclonal antibody is a bivalent antibody.

13. The method of claim 1, wherein said monoclonal antibody is a single chain antibody.

14. The method of claim 1, wherein said monoclonal antibody is humanized.

15. The method of claim 1, wherein said monoclonal antibody is a Fab, Fv, scFv, or Fd fragment.

16. The method of claim 1, wherein the monoclonal antibody comprises:
   a) an antibody variable domain comprising:
      i. a heavy chain variable domain comprising a CDR1 region identical to amino acid residues 30-35 of SEQ ID NO: 4, a CDR2 region identical to amino acid residues 50-66 of SEQ ID NO: 4 and a CDR3 region identical to amino acid residues 98-109 of SEQ ID NO: 4; and
      ii. a light chain variable domain comprising a CDR1 region identical to amino acid residues 23-35 of SEQ ID NO: 43, a CDR2 region identical to amino acid residues 51-57 of SEQ ID NO: 43 and a CDR3 region identical to amino acid residues 90-101 of SEQ ID NO: 43; or
   b) a variant of said antibody variable domain that is otherwise identical to said antibody variable domain except for up to 5 amino acid substitutions in said CDR regions.

17. The method of claim 1, wherein said monoclonal antibody comprises a variable domain comprising:
   a) a heavy chain variable domain comprising a CDR1 region identical to amino acid residues 30-35 of SEQ ID NO: 4, a CDR2 region identical to amino acid residues 50-66 of SEQ ID NO: 4 and a CDR3 region identical to amino acid residues 98-109 of SEQ ID NO: 4; and
   b) a light chain variable domain comprising a CDR1 region identical to amino acid residues 23-35 of SEQ ID NO: 43, a CDR2 region identical to amino acid residues 51-57 of SEQ ID NO: 43 and a CDR3 region identical to amino acid residues 90-101 of SEQ ID NO: 43.

18. The method of claim 1, wherein said monoclonal antibody comprises:
   a variant of said variable domain of part a) that is otherwise identical to said variable domain of part a) except for 1 to 4 amino acid substitutions in said CDR regions.

19. The method of claim 18, wherein said variant of said antibody variable domain is otherwise identical to said antibody variable domain except for a single amino acid substitution in one of said CDR regions.

* * * * *

```
                              SEQUENCE LISTING

<160> NUMBER OF SEQ ID NOS: 132

<210> SEQ ID NO 1
<211> LENGTH: 120
<212> TYPE: PRT
<213> ORGANISM: Oryctolagus cuniculus

<400> SEQUENCE: 1

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Asn Asn Ala
            20                  25                  30

Val Met Cys Trp Val Arg Gln Ala Pro Gly Lys Gly Leu Glu Trp Ile
        35                  40                  45

Gly Cys Ile Met Thr Thr Asp Val Val Thr Glu Tyr Ala Asn Trp Ala
    50                  55                  60

Lys Ser Arg Phe Thr Val Ser Lys Thr Ser Thr Thr Val Thr Leu
65                  70                  75                  80

Gln Met Thr Ser Leu Thr Val Ala Asp Thr Ala Thr Tyr Phe Cys Ala
                85                  90                  95

Arg Asp Ser Val Gly Ser Pro Leu Met Ser Phe Asp Leu Trp Gly Pro
                100                 105                 110

Gly Thr Leu Val Thr Val Ser Ser
            115                 120

<210> SEQ ID NO 2
<211> LENGTH: 120
<212> TYPE: PRT
<213> ORGANISM: Oryctolagus cuniculus

<400> SEQUENCE: 2

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Asn Asn Ala
            20                  25                  30

Val Met Cys Trp Val Arg Gln Ala Pro Gly Lys Gly Leu Glu Trp Ile
        35                  40                  45

Gly Cys Ile Met Thr Thr Asp Val Val Thr Glu Tyr Ala Asn Trp Ala
    50                  55                  60

Lys Ser Arg Phe Thr Val Ser Lys Thr Ser Thr Thr Val Thr Leu
65                  70                  75                  80

Gln Met Thr Ser Leu Thr Val Ala Asp Thr Ala Thr Tyr Phe Cys Ala
                85                  90                  95

Arg Asp Ser Val Gly Ser Pro Leu Met Ser Phe Asp Leu Trp Gly Pro
                100                 105                 110

Gly Thr Leu Val Thr Val Ser Ser
            115                 120

<210> SEQ ID NO 3
<211> LENGTH: 120
<212> TYPE: PRT
<213> ORGANISM: Oryctolagus cuniculus

<400> SEQUENCE: 3

Gln Ser Leu Glu Glu Ser Gly Gly Asp Leu Val Lys Pro Gly Ala Ser
```

```
                1               5                   10                  15
Leu Thr Leu Thr Cys Thr Ala Ser Gly Phe Ser Phe Ser Asn Asn Ala
                20                  25                  30

Val Met Cys Trp Val Arg Gln Ala Pro Gly Lys Gly Leu Glu Trp Ile
        35                  40                  45

Gly Cys Ile Met Thr Thr Asp Val Val Thr Glu Tyr Ala Asn Trp Ala
    50                  55                  60

Lys Ser Arg Phe Thr Val Ser Lys Thr Ser Ser Thr Val Thr Leu
65                  70                  75                  80

Gln Met Thr Ser Leu Thr Val Ala Asp Thr Ala Thr Tyr Phe Cys Ala
                85                  90                  95

Arg Asp Ser Val Gly Ser Pro Leu Met Ser Phe Asp Leu Trp Gly Pro
                100                 105                 110

Gly Thr Leu Val Thr Val Ser Ser
        115                 120
```

<210> SEQ ID NO 4
<211> LENGTH: 120
<212> TYPE: PRT
<213> ORGANISM: Oryctolagus cuniculus

<400> SEQUENCE: 4

```
Gln Ser Leu Glu Glu Ser Gly Gly Asp Leu Val Lys Pro Gly Ala Ser
1               5                   10                  15

Leu Thr Leu Ser Cys Thr Ala Ser Gly Phe Ser Phe Ser Asn Asn Asp
                20                  25                  30

Val Met Cys Trp Val Arg Gln Ala Pro Gly Lys Gly Leu Glu Trp Ile
        35                  40                  45

Gly Cys Ile Met Thr Thr Asp Val Val Thr Glu Tyr Ala Asn Trp Ala
    50                  55                  60

Lys Ser Arg Phe Thr Val Ser Lys Thr Ser Ser Thr Val Thr Leu
65                  70                  75                  80

Gln Leu Thr Ser Leu Thr Val Ala Asp Thr Ala Thr Tyr Phe Cys Ala
                85                  90                  95

Arg Asp Ser Val Gly Ser Pro Leu Met Ser Phe Asp Leu Trp Gly Pro
                100                 105                 110

Gly Thr Leu Val Thr Val Ser Ser
        115                 120
```

<210> SEQ ID NO 5
<211> LENGTH: 120
<212> TYPE: PRT
<213> ORGANISM: Oryctolagus cuniculus

<400> SEQUENCE: 5

```
Gln Ser Val Glu Glu Ser Gly Gly Gly Leu Val Lys Pro Gly Gly Thr
1               5                   10                  15

Leu Thr Leu Thr Cys Thr Val Ser Gly Phe Ser Phe Ser Asn Asn Asp
                20                  25                  30

Val Met Cys Trp Val Arg Gln Ala Pro Gly Lys Gly Leu Glu Trp Ile
        35                  40                  45

Gly Cys Ile Met Thr Thr Asp Val Val Thr Ala Tyr Ala Asn Trp Ala
    50                  55                  60

Lys Ser Arg Phe Thr Val Ser Arg Thr Ser Ser Thr Val Thr Leu
65                  70                  75                  80

Gln Val Thr Ser Leu Thr Val Ala Asp Thr Ala Thr Tyr Phe Cys Ala
                85                  90                  95
```

```
Arg Asp Ser Val Gly Ser Pro Leu Met Ser Phe Asp Leu Trp Gly Pro
            100                 105                 110

Gly Thr Leu Val Thr Val Ser Ser
        115                 120

<210> SEQ ID NO 6
<211> LENGTH: 117
<212> TYPE: PRT
<213> ORGANISM: Oryctolagus cuniculus

<400> SEQUENCE: 6

Gln Ser Leu Glu Glu Ser Gly Gly Gly Leu Val Gln Pro Glu Gly Ser
1               5                   10                  15

Leu Thr Leu Thr Cys Thr Ala Ser Gly Phe Ser Phe Ser Ser Ser Tyr
            20                  25                  30

Tyr Met Cys Trp Val Arg Gln Ala Pro Gly Lys Gly Leu Glu Trp Val
            35                  40                  45

Gly Cys Ile Tyr Thr Gly Ser Asn Asn Thr Tyr Tyr Ala Tyr Trp Gly
        50                  55                  60

Lys Gly Arg Phe Thr Val Thr Lys Thr Ser Thr Thr Val Thr Leu
65                  70                  75                  80

Gln Met Thr Ser Leu Thr Ala Ala Asp Thr Ala Thr Tyr Phe Cys Ala
                85                  90                  95

Arg Ala Ile Ser Ile Asn Val Tyr Val Leu Trp Gly Pro Gly Thr Leu
            100                 105                 110

Val Thr Val Ser Ser
        115

<210> SEQ ID NO 7
<211> LENGTH: 117
<212> TYPE: PRT
<213> ORGANISM: Oryctolagus cuniculus

<400> SEQUENCE: 7

Gln Ser Leu Glu Glu Ser Gly Gly Gly Leu Val Gln Pro Glu Gly Ser
1               5                   10                  15

Leu Thr Leu Thr Cys Thr Ala Ser Gly Phe Ser Phe Ser Ser Asn Tyr
            20                  25                  30

Tyr Met Cys Trp Val Arg Gln Ala Pro Gly Lys Gly Leu Glu Trp Val
            35                  40                  45

Gly Cys Ile Tyr Thr Gly Ser Asn Asn Thr Tyr Tyr Ala Ser Trp Gly
        50                  55                  60

Lys Gly Arg Phe Thr Ile Thr Lys Thr Ser Thr Thr Val Thr Leu
65                  70                  75                  80

Gln Met Thr Ser Leu Thr Ala Ala Asp Thr Ala Thr Tyr Phe Cys Thr
                85                  90                  95

Arg Gly Ile Ser Ile Asn Val Tyr Ala Leu Trp Gly Pro Gly Thr Leu
            100                 105                 110

Val Thr Val Ser Ser
        115

<210> SEQ ID NO 8
<211> LENGTH: 118
<212> TYPE: PRT
<213> ORGANISM: Oryctolagus cuniculus

<400> SEQUENCE: 8

Gln Gln Gln Leu Glu Glu Ser Gly Gly Gly Leu Val Gln Pro Glu Gly
```

```
                 1               5                  10                 15
Ser Leu Thr Leu Thr Cys Thr Ala Ser Gly Phe Ser Phe Ser Ser Gly
                20                  25                 30

Tyr Asp Met Cys Trp Val Arg Gln Val Pro Gly Lys Gly Leu Glu Trp
                35                  40                 45

Ile Gly Cys Ile Tyr Thr Gly Ser Gly Arg Thr His Tyr Ala Ser Trp
 50                 55                  60

Ala Lys Gly Arg Phe Thr Ile Ser Lys Thr Ser Ser Thr Thr Val Thr
 65                 70                  75                 80

Leu Gln Met Thr Ser Leu Thr Val Ala Asp Thr Ala Thr Tyr Phe Cys
                85                  90                 95

Ala Arg Gly Asn Ser Ile Asn Val Tyr Gly Val Trp Gly Pro Gly Thr
               100                 105                110

Leu Val Thr Val Ser Ser
               115

<210> SEQ ID NO 9
<211> LENGTH: 119
<212> TYPE: PRT
<213> ORGANISM: Oryctolagus cuniculus

<400> SEQUENCE: 9

Gln Ser Leu Glu Glu Ser Gly Gly Gly Leu Val Gln Pro Glu Gly Ser
 1              5                   10                 15

Leu Thr Leu Thr Cys Thr Ala Ser Gly Phe Asp Leu Ser Ser Tyr Tyr
                20                  25                 30

Tyr Met Cys Trp Val Arg Gln Ala Pro Gly Lys Gly Leu Glu Trp Ile
                35                  40                 45

Gly Cys Ile Glu Thr Gly Ser Gly Ala Thr Ala Tyr Ala Asn Trp Ala
 50                 55                  60

Lys Gly Arg Phe Thr Val Ser Lys Thr Ser Thr Thr Val Thr Leu
 65                 70                  75                 80

Gln Val Thr Ser Leu Thr Ala Ala Asp Thr Ala Thr Tyr Phe Cys Ala
                85                  90                 95

Arg Asn Pro Tyr Ala Ser Ser Ser Gln Asn Leu Trp Gly Pro Gly
               100                 105                110

Thr Leu Val Thr Val Ser Ser
               115

<210> SEQ ID NO 10
<211> LENGTH: 120
<212> TYPE: PRT
<213> ORGANISM: Oryctolagus cuniculus

<400> SEQUENCE: 10

Gln Glu Gln Leu Glu Glu Ser Gly Gly Gly Leu Val Lys Pro Glu Gly
 1              5                   10                 15

Ser Leu Thr Leu Thr Cys Thr Ala Ser Gly Phe Ser Phe Ser Ser Ser
                20                  25                 30

Tyr Asn Met Cys Trp Val Arg Gln Ala Pro Gly Lys Gly Pro Glu Trp
                35                  40                 45

Ile Ala Cys Ile His Gly Gly Asp Gly Thr Thr Tyr Tyr Ala Thr
 50                 55                  60

Trp Ala Lys Gly Arg Phe Thr Ile Ser Lys Thr Ser Ser Thr Thr Val
 65                 70                  75                 80

Thr Leu Gln Met Thr Ser Leu Thr Ala Ala Asp Thr Ala Thr Tyr Phe
                85                  90                 95
```

```
Cys Val Arg Asp Glu Trp Ala Gly Thr Arg Leu Lys Leu Trp Gly Pro
                100                 105                 110

Gly Thr Leu Leu Thr Val Ser Ser
        115                 120

<210> SEQ ID NO 11
<211> LENGTH: 119
<212> TYPE: PRT
<213> ORGANISM: Oryctolagus cuniculus

<400> SEQUENCE: 11

Gln Ser Leu Glu Glu Ser Gly Gly Gly Leu Val Lys Pro Gly Gly Thr
1               5                   10                  15

Leu Thr Leu Thr Cys Lys Ala Ser Gly Phe Ser Phe Ser Ser Ser Tyr
            20                  25                  30

Asn Ile Cys Trp Val Arg Gln Ala Pro Gly Lys Gly Leu Glu Trp Ile
        35                  40                  45

Ala Cys Ile His Gly Gly Ser Asp Gly Thr Thr Tyr Tyr Ala Thr Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Asp Glu Trp Ala Gly Thr Arg Leu Asn Leu Trp Gly Pro Gly
                100                 105                 110

Thr Leu Val Thr Val Ser Ser
        115

<210> SEQ ID NO 12
<211> LENGTH: 116
<212> TYPE: PRT
<213> ORGANISM: Oryctolagus cuniculus

<400> SEQUENCE: 12

Gln Ser Leu Glu Glu Ser Gly Gly Asp Leu Val Gln Pro Glu Gly Ser
1               5                   10                  15

Leu Thr Leu Thr Cys Lys Ala Ser Gly Phe Asp Phe Ser Ser Asn Ala
            20                  25                  30

Met Cys Trp Val Arg Gln Ala Pro Gly Lys Gly Pro Glu Trp Ile Ala
        35                  40                  45

Trp Ile Tyr Tyr Gly Asp Val Ser Ala Tyr Tyr Ala Ser Trp Ala Lys
    50                  55                  60

Gly Arg Phe Thr Ile Ser Lys Thr Ser Ser Thr Thr Val Thr Leu Gln
65                  70                  75                  80

Met Thr Ser Leu Thr Ala Ala Asp Thr Ala Thr Tyr Phe Cys Ala Arg
                85                  90                  95

Asn Leu Gly Ala Gly Thr Leu Asp Leu Trp Gly Pro Gly Thr Leu Val
                100                 105                 110

Thr Val Ser Ser
        115

<210> SEQ ID NO 13
<211> LENGTH: 119
<212> TYPE: PRT
<213> ORGANISM: Oryctolagus cuniculus

<400> SEQUENCE: 13

Gln Gln Gln Leu Glu Glu Ser Gly Gly Gly Leu Val Lys Pro Gly Gly
```

```
              1               5                  10                 15
            Thr Leu Thr Leu Thr Cys Lys Ala Ser Gly Ile Asp Phe Ser Ser Asn
                            20                  25                  30

Tyr Tyr Met Cys Trp Val Arg Gln Ala Pro Gly Lys Gly Leu Glu Trp
                        35                  40                  45

Ile Gly Cys Ile Phe Pro Asp Tyr Gly Thr Thr Glu Tyr Ala Ser Trp
                    50                  55                  60

Ala Arg Gly Arg Phe Thr Ile Ser Lys Thr Ser Ser Thr Thr Val Thr
            65                  70                  75                  80

Leu Gln Met Thr Ser Leu Thr Ala Ala Asp Thr Ala Thr Tyr Phe Cys
                            85                  90                  95

Gly Arg Tyr Ile Leu Gly Ser Asn Val Tyr Asn Leu Trp Gly Pro Gly
                        100                 105                 110

Thr Leu Val Thr Val Ser Ser
                        115

<210> SEQ ID NO 14
<211> LENGTH: 119
<212> TYPE: PRT
<213> ORGANISM: Oryctolagus cuniculus

<400> SEQUENCE: 14

Gln Glu Gln Leu Val Glu Phe Gly Gly Gly Leu Val Gln Pro Glu Gly
            1               5                   10                  15

Ala Leu Thr Leu Thr Cys Thr Ala Ser Glu Phe Ser Phe Ser Ser Gly
                            20                  25                  30

His Tyr Met Cys Trp Val Arg Gln Ala Pro Gly Lys Gly Leu Glu Trp
                        35                  40                  45

Ile Ala Cys Ile Asn Thr Gly Ser Gly Met Thr Trp Tyr Ala Asn Trp
                    50                  55                  60

Ala Lys Gly Arg Phe Thr Ile Ser Arg Ser Thr Ser Leu Asn Thr Val
            65                  70                  75                  80

Asp Leu Lys Val Thr Ser Leu Thr Val Ala Asp Thr Ala Thr Tyr Phe
                            85                  90                  95

Cys Ala Arg Gly Asp Asn Gly Trp Pro Phe Asp Leu Trp Gly Pro Gly
                        100                 105                 110

Thr Leu Val Thr Val Ser Ser
                        115

<210> SEQ ID NO 15
<211> LENGTH: 123
<212> TYPE: PRT
<213> ORGANISM: Oryctolagus cuniculus

<400> SEQUENCE: 15

Gln Glu Gln Leu Lys Glu Thr Gly Gly Gly Leu Val Thr Pro Gly Gly
            1               5                   10                  15

Asn Leu Ala Leu Ser Cys Thr Ala Ser Gly Phe Asp Phe Asn Ser Asp
                            20                  25                  30

Trp Met Gly Trp Val Arg Gln Ala Pro Gly Lys Gly Leu Glu Trp Ile
                        35                  40                  45

Gly Asp Ile Ser Gly Arg Val Asp Thr Thr Ala Tyr Ala Ser Trp Val
                    50                  55                  60

Asn Gly Arg Phe Thr Ile Ser Ser Asp Asn Ala Gln Asn Thr Val Asp
            65                  70                  75                  80

Leu Gln Met Asn Arg Leu Thr Ala Ala Asp Thr Gly Thr Tyr Phe Cys
                            85                  90                  95
```

Ala Arg Ile Ala Arg Tyr Ile Asp Ser Val Tyr Tyr Phe Asp Leu
            100                 105                 110

Trp Gly Pro Gly Thr Leu Val Thr Val Ser Ser
            115                 120

<210> SEQ ID NO 16
<211> LENGTH: 116
<212> TYPE: PRT
<213> ORGANISM: Oryctolagus cuniculus

<400> SEQUENCE: 16

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Thr Tyr Glu
            20                  25                  30

Gly Ser Trp Val Arg Gln Ala Pro Gly Lys Gly Leu Glu Trp Ile Gly
            35                  40                  45

Tyr Ile Tyr Thr Asp Ser Asp Thr Val Tyr Ala Thr Trp Ala Lys Gly
        50                  55                  60

Arg Phe Ala Ile Ser Lys Met Ser Thr Thr Val Glu Leu Lys Ile Thr
65                  70                  75                  80

Ser Pro Thr Thr Glu Asp Thr Ala Thr Tyr Phe Cys Thr Arg Gly Asp
                85                  90                  95

Leu Ser Ser Gly Trp Gly Ala Ala Leu Trp Gly Pro Gly Thr Leu Val
            100                 105                 110

Thr Val Ser Ser
            115

<210> SEQ ID NO 17
<211> LENGTH: 116
<212> TYPE: PRT
<213> ORGANISM: Oryctolagus cuniculus

<400> SEQUENCE: 17

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Tyr Glu
            20                  25                  30

Gly Asn Trp Val Arg Gln Ala Pro Gly Lys Gly Leu Glu Trp Ile Gly
            35                  40                  45

Tyr Ile Tyr Pro Asp Gly Asp Thr Val Tyr Ala Ser Trp Ala Lys Gly
        50                  55                  60

Arg Phe Thr Ile Ser Lys Met Ser Thr Thr Val Asp Leu Lys Ile Thr
65                  70                  75                  80

Ser Pro Thr Thr Glu Asp Thr Ala Thr Tyr Phe Cys Thr Thr Asp
                85                  90                  95

Leu Asn Thr Gly Trp Gly Ala Asn Leu Trp Gly Pro Gly Thr Leu Val
            100                 105                 110

Thr Val Ser Ser
            115

<210> SEQ ID NO 18
<211> LENGTH: 116
<212> TYPE: PRT
<213> ORGANISM: Oryctolagus cuniculus

<400> SEQUENCE: 18

Gln Ser Val Glu Glu Ser Gly Gly Arg Leu Val Thr Pro Gly Thr Pro

```
            1               5                   10                  15
Leu Thr Leu Thr Cys Thr Val Ser Gly Phe Ser Leu Ser Ile Tyr Glu
            20                  25                  30

Met Ser Trp Val Arg Gln Ala Pro Gly Lys Gly Leu Glu Trp Ile Gly
            35                  40                  45

Tyr Ile Tyr Thr Asp Gly Asp Thr Val Tyr Ala Ser Trp Ala Lys Gly
            50                  55                  60

Arg Phe Thr Ile Ser Lys Met Ser Thr Thr Val Asp Leu Lys Ile Thr
65                  70                  75                  80

Ser Pro Thr Thr Glu Asp Thr Ala Thr Tyr Phe Cys Thr Arg Gly Asp
            85                  90                  95

Leu Ser Ser Gly Trp Gly Ala Asn Leu Trp Gly Pro Gly Thr Leu Val
            100                 105                 110

Thr Val Ser Ser
            115
```

<210> SEQ ID NO 19
<211> LENGTH: 116
<212> TYPE: PRT
<213> ORGANISM: Oryctolagus cuniculus

<400> SEQUENCE: 19

```
Gln Ser Val Glu Glu Ser Gly Gly Arg Leu Val Thr Pro Gly Thr Pro
1               5                   10                  15

Leu Thr Leu Ser Cys Thr Val Ser Gly Phe Ser Leu Ser Val Tyr Glu
            20                  25                  30

Met Ser Trp Val Arg Gln Ala Pro Gly Lys Gly Leu Gln Trp Ile Gly
            35                  40                  45

Val Ile Tyr Ser Asp Gly Ser Thr Val Tyr Ala Ser Trp Ala Lys Gly
            50                  55                  60

Arg Phe Thr Ile Ser Lys Met Ser Thr Thr Val Asp Leu Lys Ile Thr
65                  70                  75                  80

Ser Pro Thr Thr Glu Asp Thr Ala Thr Tyr Phe Cys Thr Arg Gly Asp
            85                  90                  95

Leu Asn Thr Gly Trp Gly Ala Asp Leu Trp Gly Pro Gly Thr Leu Val
            100                 105                 110

Thr Val Ser Ser
            115
```

<210> SEQ ID NO 20
<211> LENGTH: 116
<212> TYPE: PRT
<213> ORGANISM: Oryctolagus cuniculus

<400> SEQUENCE: 20

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Tyr Tyr
            20                  25                  30

Trp Asn Trp Val Arg Gln Ala Pro Gly Glu Gly Leu Glu Trp Ile Gly
            35                  40                  45

Phe Ile Asp Leu Leu Gly Ser Ala Asp Tyr Ala Ser Trp Ala Lys Gly
            50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Thr Arg Ser Gly
            85                  90                  95
```

```
Ser His Ser Gly Trp Gly Ala Asp Ile Trp Gly Pro Gly Thr Leu Val
            100                 105                 110

Thr Val Ser Ser
        115

<210> SEQ ID NO 21
<211> LENGTH: 116
<212> TYPE: PRT
<213> ORGANISM: Oryctolagus cuniculus

<400> SEQUENCE: 21

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Tyr Tyr
            20                  25                  30

Trp Asn Trp Val Arg Gln Ala Pro Gly Glu Gly Leu Glu Trp Ile Gly
            35                  40                  45

Phe Ile Asp Leu Leu Gly Ser Ala Asp Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Thr Arg Ser Gly
                85                  90                  95

Ser His Ser Gly Trp Gly Ala Asp Ile Trp Gly Pro Gly Thr Leu Val
            100                 105                 110

Thr Val Ser Ser
        115

<210> SEQ ID NO 22
<211> LENGTH: 116
<212> TYPE: PRT
<213> ORGANISM: Oryctolagus cuniculus

<400> SEQUENCE: 22

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Tyr Tyr
            20                  25                  30

Trp Asn Trp Val Arg Gln Ala Pro Gly Glu Gly Leu Glu Trp Ile Gly
            35                  40                  45

Phe Ile Asp Leu Leu Gly Ser Ala Asp Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Thr Arg Ser Gly
                85                  90                  95

Ser His Ser Gly Trp Cys Ala Asp Ile Trp Gly Pro Gly Thr Leu Val
            100                 105                 110

Thr Val Ser Ser
        115

<210> SEQ ID NO 23
<211> LENGTH: 116
<212> TYPE: PRT
<213> ORGANISM: Oryctolagus cuniculus

<400> SEQUENCE: 23

Gln Ser Val Glu Glu Ser Gly Gly Arg Leu Val Thr Pro Gly Thr Pro
```

```
                1               5                   10                  15
Leu Thr Leu Thr Cys Thr Ala Ser Gly Phe Ser Leu Ser Asn Tyr Tyr
            20                  25                  30

Trp Asn Trp Val Arg Gln Ala Pro Gly Glu Gly Leu Glu Trp Ile Gly
        35                  40                  45

Phe Ile Asp Leu Leu Gly Ser Ala Asp Tyr Ala Ser Trp Ala Lys Gly
    50                  55                  60

Arg Phe Thr Ile Ser Lys Thr Ser Thr Val Asp Leu Lys Ile Thr
65                  70                  75                  80

Ser Pro Thr Thr Glu Asp Thr Ala Thr Tyr Phe Cys Ala Arg Ser Gly
                85                  90                  95

Ser Ser Ser Gly Trp Gly Ala Asp Ile Trp Gly Pro Gly Thr Leu Val
            100                 105                 110

Thr Val Ser Ser
            115

<210> SEQ ID NO 24
<211> LENGTH: 116
<212> TYPE: PRT
<213> ORGANISM: Oryctolagus cuniculus

<400> SEQUENCE: 24

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Tyr
            20                  25                  30

Met Asn Trp Val Arg Gln Ala Pro Gly Lys Gly Leu Glu Trp Ile Gly
        35                  40                  45

Phe Ile Asp Phe Ser Ser Asp Ala Tyr Tyr Ala Asn Trp Ala Lys Gly
    50                  55                  60

Arg Phe Thr Ile Ser Arg Thr Ser Thr Val Asp Leu Lys Met Thr
65                  70                  75                  80

Ser Leu Thr Ser Glu Asp Thr Ala Thr Tyr Phe Cys Ala Ser Ser Gly
                85                  90                  95

Val Asp Ser Ala Trp Gly Phe Asp Leu Trp Gly Pro Gly Thr Leu Val
            100                 105                 110

Thr Val Ser Ser
            115

<210> SEQ ID NO 25
<211> LENGTH: 116
<212> TYPE: PRT
<213> ORGANISM: Oryctolagus cuniculus

<400> SEQUENCE: 25

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Tyr
            20                  25                  30

Met Asn Trp Val Arg Gln Ala Pro Gly Lys Gly Leu Glu Trp Ile Gly
        35                  40                  45

Phe Ile Asp Phe Gly Ser Asp Ala Tyr Tyr Ala Asn Trp Ala Lys Gly
    50                  55                  60

Arg Phe Thr Ile Ser Arg Thr Ser Thr Thr Val Asp Leu Lys Met Thr
65                  70                  75                  80

Ser Leu Thr Ser Glu Asp Thr Ala Thr Tyr Phe Cys Ala Arg Ser Gly
                85                  90                  95
```

Val Asp Ser Gly Trp Gly Phe Asp Leu Trp Gly Pro Gly Thr Leu Val
            100                 105                 110
Thr Val Ser Ser
        115

<210> SEQ ID NO 26
<211> LENGTH: 116
<212> TYPE: PRT
<213> ORGANISM: Oryctolagus cuniculus

<400> SEQUENCE: 26

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Tyr
            20                  25                  30

Met Ser Trp Val Arg Gln Ala Pro Gly Lys Gly Leu Glu Trp Ile Gly
        35                  40                  45

Phe Ile Asp Phe Ser Ser Asp Ala Tyr Tyr Ala Asn Trp Ala Lys Gly
    50                  55                  60

Arg Phe Thr Ile Ser Arg Thr Ser Thr Thr Val Asp Leu Lys Met Thr
65                  70                  75                  80

Ser Leu Thr Ser Glu Asp Thr Ala Thr Tyr Phe Cys Ala Arg Ser Gly
                85                  90                  95

Val Asp Ser Gly Trp Gly Phe Asp Leu Trp Gly Pro Gly Thr Leu Val
            100                 105                 110

Thr Val Ser Ser
        115

<210> SEQ ID NO 27
<211> LENGTH: 118
<212> TYPE: PRT
<213> ORGANISM: Oryctolagus cuniculus

<400> SEQUENCE: 27

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Trp
            20                  25                  30

Met Ser Trp Val Arg Gln Ala Pro Gly Glu Gly Leu Glu Trp Ile Gly
        35                  40                  45

Thr Ile Ser Thr Ala Asn Asn Thr Tyr Tyr Ala Asn Trp Ala Met Gly
    50                  55                  60

Arg Phe Thr Ile Ser Arg Thr Ser Thr Thr Val Asp Leu Lys Met Thr
65                  70                  75                  80

Ser Pro Thr Ser Glu Asp Thr Ala Thr Tyr Phe Cys Ala Arg Ser Asn
                85                  90                  95

Val Leu Lys Arg Ile Gly Asp Arg Phe Asp Leu Trp Gly Pro Gly Thr
            100                 105                 110

Leu Val Thr Val Ser Ser
        115

<210> SEQ ID NO 28
<211> LENGTH: 115
<212> TYPE: PRT
<213> ORGANISM: Oryctolagus cuniculus

<400> SEQUENCE: 28

Gln Ser Leu Glu Glu Ser Gly Gly Arg Leu Val Thr Pro Gly Thr Pro

```
                1               5                   10                  15
Leu Thr Leu Thr Cys Thr Ala Ser Gly Phe Ser Leu Asn Asn Tyr Tyr
                    20                  25                  30

Met Asn Trp Val Arg Gln Ala Pro Gly Lys Gly Leu Glu Trp Ile Gly
            35                  40                  45

Ile Ile Asp Ile Val Gly Ser Thr Tyr Tyr Ala Asn Trp Ala Lys Gly
    50                  55                  60

Arg Phe Thr Ile Ser Arg Thr Ser Thr Thr Val Asp Leu Lys Met Thr
65                  70                  75                  80

Ser Leu Thr Thr Glu Asp Thr Ala Thr Tyr Phe Cys Ala Arg Thr Asp
                85                  90                  95

Thr Asn Tyr Trp Ala His Asp Leu Trp Gly Pro Gly Thr Leu Val Thr
            100                 105                 110

Val Ser Ser
        115

<210> SEQ ID NO 29
<211> LENGTH: 117
<212> TYPE: PRT
<213> ORGANISM: Oryctolagus cuniculus

<400> SEQUENCE: 29

Gln Ser Val Glu Glu Ser Gly Gly Arg Leu Val Thr Pro Gly Thr Pro
1               5                   10                  15

Leu Thr Leu Thr Cys Thr Ala Ser Arg Phe Ser Leu Ser Ser Tyr Asp
                20                  25                  30

Met Ile Trp Val Arg Gln Ala Pro Gly Lys Gly Leu Glu Trp Ile Gly
            35                  40                  45

Tyr Ile Asp Ala Val Gly Ser Ser Thr Tyr Tyr Ala Ser Trp Ala Lys
    50                  55                  60

Gly Arg Phe Thr Ile Ser Lys Thr Ser Thr Thr Val Asp Leu Lys Met
65                  70                  75                  80

Thr Ser Pro Thr Thr Glu Asp Thr Ala Thr Tyr Phe Cys Ala Arg Gly
                85                  90                  95

Asp Trp Ser Thr Ala Trp Gly Phe Asn Leu Trp Gly Pro Gly Thr Leu
            100                 105                 110

Val Thr Val Ser Ser
        115

<210> SEQ ID NO 30
<211> LENGTH: 117
<212> TYPE: PRT
<213> ORGANISM: Oryctolagus cuniculus

<400> SEQUENCE: 30

Gln Ser Val Glu Glu Ser Gly Gly Arg Leu Val Thr Pro Gly Thr Pro
1               5                   10                  15

Leu Thr Leu Thr Cys Thr Ala Ser Arg Phe Ser Leu Ser Ser Tyr Asp
                20                  25                  30

Ile Ile Trp Val Arg Gln Ala Pro Gly Lys Gly Leu Glu Trp Ile Gly
            35                  40                  45

Tyr Ile Asp Thr Val Gly Ser Ser Thr Tyr Tyr Ala Ser Trp Ala Lys
    50                  55                  60

Gly Arg Phe Thr Ile Ser Lys Thr Ser Thr Thr Val Asp Leu Lys Met
65                  70                  75                  80

Thr Ser Pro Thr Thr Glu Asp Thr Ala Thr Tyr Phe Cys Ala Arg Gly
                85                  90                  95
```

```
Asp Trp Ser Thr Ala Trp Gly Phe Asn Leu Trp Gly Pro Gly Thr Leu
            100                 105                 110
Val Thr Val Ser Ser
        115

<210> SEQ ID NO 31
<211> LENGTH: 117
<212> TYPE: PRT
<213> ORGANISM: Oryctolagus cuniculus

<400> SEQUENCE: 31

Gln Ser Val Glu Glu Ser Gly Gly Arg Leu Val Thr Pro Gly Thr Pro
1               5                   10                  15
Leu Thr Leu Thr Cys Thr Ala Ser Arg Phe Ser Leu Ser Ser Tyr Asp
            20                  25                  30
Met Ile Trp Val Arg Gln Ala Pro Gly Lys Gly Leu Glu Trp Ile Gly
        35                  40                  45
Tyr Ile Asp Thr Ile Gly Ser Ser Arg Tyr Tyr Ala Ser Trp Ala Lys
    50                  55                  60
Gly Arg Phe Thr Ile Ser Lys Thr Ser Thr Thr Val Asp Leu Lys Met
65                  70                  75                  80
Thr Ser Pro Thr Thr Glu Asp Thr Ala Thr Tyr Phe Cys Ala Arg Gly
                85                  90                  95
Asp Trp Ser Thr Ala Trp Gly Phe Asn Leu Trp Gly Pro Gly Thr Leu
            100                 105                 110
Val Thr Val Ser Ser
        115

<210> SEQ ID NO 32
<211> LENGTH: 120
<212> TYPE: PRT
<213> ORGANISM: Oryctolagus cuniculus

<400> SEQUENCE: 32

Gln Ser Val Glu Glu Ser Gly Gly Arg Leu Val Thr Pro Gly Thr Pro
1               5                   10                  15
Leu Thr Leu Thr Cys Thr Val Ser Gly Phe Ser Leu Ser Ser Tyr Ala
            20                  25                  30
Val Ser Trp Val Arg Gln Ala Pro Gly Lys Gly Leu Glu Trp Ile Gly
        35                  40                  45
Ile Ile Ser Ser Ser Gly Ser Thr Tyr Tyr Ala Ser Trp Ala Lys Gly
    50                  55                  60
Arg Phe Thr Gly Ser Arg Thr Ser Thr Thr Val Asp Leu Lys Ile Thr
65                  70                  75                  80
Ser Pro Thr Thr Glu Asp Thr Ala Thr Tyr Phe Cys Ala Arg Asp Ala
                85                  90                  95
Asn Ser Arg Gly Tyr Tyr Ile Pro Tyr Tyr Phe Asn Ile Trp Gly Pro
            100                 105                 110
Gly Thr Leu Val Thr Val Ser Ser
        115                 120

<210> SEQ ID NO 33
<211> LENGTH: 120
<212> TYPE: PRT
<213> ORGANISM: Oryctolagus cuniculus

<400> SEQUENCE: 33

Gln Ser Val Glu Glu Ser Gly Gly Arg Leu Val Thr Pro Gly Thr Pro
```

```
                1               5                  10                 15
Leu Thr Leu Thr Cys Thr Val Ser Gly Phe Ser Leu Ser Ser Tyr Ala
                20                 25                 30

Val Ser Trp Val Arg Gln Ala Pro Gly Lys Gly Leu Glu Trp Ile Gly
            35                 40                 45

Ile Ile Ser Ser Ser Gly Ser Thr Tyr Tyr Ala Ser Trp Ala Lys Gly
        50                 55                 60

Arg Phe Thr Gly Ser Arg Thr Ser Thr Val Asp Leu Lys Ile Thr
65                 70                 75                 80

Ser Pro Thr Thr Glu Asp Thr Ala Thr Tyr Phe Cys Ala Arg Asp Ala
                85                 90                 95

Asn Ser Arg Gly Tyr Tyr Ile Pro Tyr Phe Asn Ile Trp Gly Pro
                100                105                110

Gly Thr Leu Val Thr Val Ser Ser
            115                120

<210> SEQ ID NO 34
<211> LENGTH: 120
<212> TYPE: PRT
<213> ORGANISM: Oryctolagus cuniculus

<400> SEQUENCE: 34

Gln Ser Val Glu Glu Ser Gly Gly Arg Leu Val Thr Pro Gly Thr Pro
1               5                  10                 15

Leu Thr Leu Thr Cys Thr Val Ser Gly Phe Ser Leu Ser Ser Tyr Ala
                20                 25                 30

Met Ser Trp Val Arg Gln Ala Pro Gly Lys Gly Leu Glu Trp Ile Gly
            35                 40                 45

Ile Ile Thr Ser Ser Val Ile Thr Tyr Tyr Ala Ser Trp Ala Lys Gly
        50                 55                 60

Arg Phe Thr Ile Ser Lys Thr Ser Thr Val Asp Leu Lys Ile Thr
65                 70                 75                 80

Ser Pro Thr Thr Glu Asp Thr Ala Thr Tyr Phe Cys Ala Arg Asp Ala
                85                 90                 95

Ser Ser Thr Gly Tyr Tyr Ile Pro Tyr Phe Asn Ile Trp Gly Pro
                100                105                110

Gly Thr Leu Val Thr Val Ser Ser
            115                120

<210> SEQ ID NO 35
<211> LENGTH: 114
<212> TYPE: PRT
<213> ORGANISM: Oryctolagus cuniculus

<400> SEQUENCE: 35

Gln Ser Val Glu Glu Ser Gly Gly Arg Leu Val Thr Pro Gly Thr Pro
1               5                  10                 15

Leu Thr Leu Thr Cys Thr Val Ser Gly Phe Ser Leu Ser Ser Tyr Ala
                20                 25                 30

Met Ser Trp Val Arg Gln Ala Pro Gly Lys Gly Leu Glu Trp Ile Gly
            35                 40                 45

Ile Ile Tyr Ala Ser Gly Ser Thr Tyr Tyr Ala Ser Trp Ala Lys Gly
        50                 55                 60

Arg Phe Thr Ile Ser Lys Thr Ser Thr Val Asp Leu Lys Met Thr
65                 70                 75                 80

Ser Leu Thr Ile Glu Asp Thr Ala Thr Tyr Phe Cys Gly Arg Gly Tyr
                85                 90                 95
```

```
Pro Ala Tyr Asp Thr Phe Leu Trp Gly Pro Gly Thr Leu Val Thr Val
                100                 105                 110

Ser Ser

<210> SEQ ID NO 36
<211> LENGTH: 114
<212> TYPE: PRT
<213> ORGANISM: Oryctolagus cuniculus

<400> SEQUENCE: 36

Gln Ser Leu Glu Glu Ser Gly Gly Arg Leu Val Thr Pro Gly Thr Pro
1               5                   10                  15

Leu Thr Leu Thr Cys Lys Val Ser Gly Ile Asp Leu Asn Ser Tyr Ala
                20                  25                  30

Met Gly Trp Phe Arg Lys Ala Pro Gly Lys Gly Leu Glu Trp Ile Gly
            35                  40                  45

Ile Ile Tyr Leu Glu Thr Gly Asn Thr Tyr Tyr Ala Thr Trp Ala Lys
        50                  55                  60

Gly Arg Phe Thr Ile Ser Lys Thr Ser Thr Thr Val Asp Leu Gly Ile
65                  70                  75                  80

Thr Ser Pro Thr Thr Glu Asp Thr Ala Thr Tyr Phe Cys Ala Arg Gly
                85                  90                  95

Ser Trp Ser Asp Tyr Ala Leu Trp Gly Pro Gly Thr Leu Val Thr Val
                100                 105                 110

Ser Ser

<210> SEQ ID NO 37
<211> LENGTH: 114
<212> TYPE: PRT
<213> ORGANISM: Oryctolagus cuniculus

<400> SEQUENCE: 37

Gln Ser Leu Glu Glu Ser Gly Gly Arg Leu Val Thr Pro Gly Thr Pro
1               5                   10                  15

Leu Thr Leu Thr Cys Lys Val Ser Gly Ile Asp Leu Asn Ser Tyr Ala
                20                  25                  30

Met Gly Trp Phe Arg Lys Ala Pro Gly Lys Gly Leu Glu Trp Ile Gly
            35                  40                  45

Ile Ile Tyr Leu Glu Thr Gly Asn Thr Tyr Tyr Ala Thr Trp Ala Lys
        50                  55                  60

Gly Arg Phe Thr Ile Ser Lys Thr Ser Thr Thr Val Asp Leu Gly Ile
65                  70                  75                  80

Thr Ser Pro Thr Thr Glu Asp Thr Ala Thr Tyr Phe Cys Ala Arg Gly
                85                  90                  95

Ser Trp Ser Asp Tyr Ala Leu Trp Gly Pro Gly Thr Leu Val Thr Val
                100                 105                 110

Ser Ser

<210> SEQ ID NO 38
<211> LENGTH: 118
<212> TYPE: PRT
<213> ORGANISM: Oryctolagus cuniculus

<400> SEQUENCE: 38

Gln Ser Leu Glu Glu Ser Gly Gly Arg Leu Ile Thr Pro Gly Thr Pro
1               5                   10                  15

Leu Thr Leu Thr Cys Thr Val Ser Gly Phe Ser Leu Ser Ser Tyr Asp
```

```
                20                  25                  30
Met Ser Trp Val Arg Gln Ala Pro Gly Lys Gly Leu Glu Trp Ile Glu
            35                  40                  45

Thr Ile Ser Ser His Asp Asn Thr Trp Tyr Ala Ser Trp Ala Lys Gly
        50                  55                  60

Arg Phe Thr Ile Ser Lys Thr Ser Ser Thr Thr Val Asp Leu Arg Ile
 65                  70                  75                  80

Thr Ser Pro Thr Thr Glu Asp Thr Ala Thr Tyr Phe Cys Ala Arg Gly
                85                  90                  95

Tyr Ile Thr Gly Asn Ser Phe Tyr Phe Ser Ser Trp Gly Pro Gly Thr
            100                 105                 110

Leu Val Thr Val Ser Ser
            115

<210> SEQ ID NO 39
<211> LENGTH: 111
<212> TYPE: PRT
<213> ORGANISM: Oryctolagus cuniculus

<400> SEQUENCE: 39

Leu Val Met Thr Gln Thr Pro Ala Ser Val Ser Ala Ala Val Gly Gly
 1               5                  10                  15

Thr Val Thr Ile Asn Cys Gln Ala Ser Gln Asn Leu Tyr Asn Asn Asn
            20                  25                  30

Glu Leu Ser Trp Tyr Gln Gln Lys Pro Gly Gln Pro Pro Lys Leu Leu
        35                  40                  45

Ile Tyr Trp Ala Ser Thr Leu Ala Ser Gly Val Pro Ser Arg Phe Lys
 50                  55                  60

Gly Ser Gly Ser Gly Thr Gln Phe Thr Leu Thr Ile Ser Gly Val Gln
 65                  70                  75                  80

Cys Ala Asp Ala Ala Thr Tyr Tyr Cys Ala Gly Tyr Lys Ser Tyr Ser
                85                  90                  95

Asn Asp Gly Asn Gly Phe Gly Gly Gly Thr Glu Val Val Val Lys
            100                 105                 110

<210> SEQ ID NO 40
<211> LENGTH: 111
<212> TYPE: PRT
<213> ORGANISM: Oryctolagus cuniculus

<400> SEQUENCE: 40

Leu Val Met Thr Gln Thr Pro Ala Ser Val Ser Ala Ala Val Gly Gly
 1               5                  10                  15

Thr Val Thr Ile Asn Cys Gln Ala Ser Gln Asn Leu Tyr Asn Asn Asn
            20                  25                  30

Glu Leu Ser Trp Tyr Gln Gln Lys Pro Gly Gln Pro Pro Lys Leu Leu
        35                  40                  45

Ile Tyr Trp Ala Ser Thr Leu Ala Ser Gly Val Pro Ser Arg Phe Lys
 50                  55                  60

Gly Ser Gly Ser Gly Thr Gln Phe Thr Leu Thr Ile Ser Gly Val Gln
 65                  70                  75                  80

Cys Ala Asp Ala Ala Thr Tyr Tyr Cys Ala Gly Tyr Lys Ser Tyr Ser
                85                  90                  95

Asn Asp Gly Asn Gly Phe Gly Gly Gly Thr Glu Val Val Val Lys
            100                 105                 110

<210> SEQ ID NO 41
```

```
<211> LENGTH: 111
<212> TYPE: PRT
<213> ORGANISM: Oryctolagus cuniculus

<400> SEQUENCE: 41

Leu Val Met Thr Gln Thr Pro Ala Ser Val Ser Ala Ala Val Gly Gly
1               5                   10                  15

Thr Val Ile Ile Asn Cys Gln Ala Ser Gln Asn Leu Tyr Asn Asn Asn
            20                  25                  30

Glu Leu Ser Trp Tyr Gln Gln Lys Pro Gly Gln Pro Pro Lys Leu Leu
        35                  40                  45

Ile Tyr Trp Ala Ser Thr Leu Ala Ser Gly Val Pro Ser Arg Phe Lys
    50                  55                  60

Gly Ser Gly Ser Gly Thr Gln Phe Thr Leu Thr Ile Ser Gly Val Gln
65                  70                  75                  80

Cys Ala Asp Ala Ala Thr Tyr Tyr Cys Ala Gly Tyr Lys Ser Tyr Ser
                85                  90                  95

Asn Gly Gly Asn Gly Phe Gly Gly Gly Thr Glu Val Val Val Lys
            100                 105                 110

<210> SEQ ID NO 42
<211> LENGTH: 111
<212> TYPE: PRT
<213> ORGANISM: Oryctolagus cuniculus

<400> SEQUENCE: 42

Leu Val Met Thr Gln Thr Pro Ala Ser Val Ser Ala Ala Val Gly Gly
1               5                   10                  15

Thr Val Thr Ile Asn Cys Gln Ala Ser Gln Ser Val Tyr Gly Asn Asn
            20                  25                  30

Glu Leu Ser Trp Tyr Gln Gln Lys Pro Gly Gln Arg Pro Lys Leu Leu
        35                  40                  45

Ile Tyr Arg Ala Ser Thr Leu Ala Ser Gly Val Pro Ser Arg Phe Ser
    50                  55                  60

Gly Ser Gly Ser Gly Thr Gln Phe Thr Leu Thr Ile Ser Gly Val Gln
65                  70                  75                  80

Cys Phe Asp Ala Ala Thr Tyr Tyr Cys Ser Gly Tyr Lys Ser Tyr Tyr
                85                  90                  95

Asn Asp Gly Ser Gly Phe Gly Gly Gly Thr Glu Val Val Val Lys
            100                 105                 110

<210> SEQ ID NO 43
<211> LENGTH: 111
<212> TYPE: PRT
<213> ORGANISM: Oryctolagus cuniculus

<400> SEQUENCE: 43

Leu Val Met Thr Gln Thr Pro Ala Ser Val Ser Ala Ala Val Gly Gly
1               5                   10                  15

Thr Val Thr Ile Asn Cys Gln Ala Ser Gln Ser Val Tyr Gly Asn Asn
            20                  25                  30

Glu Leu Ser Trp Tyr Gln Gln Lys Pro Gly Gln Pro Pro Lys Leu Leu
        35                  40                  45

Ile Tyr Arg Ala Ser Thr Leu Ala Ser Gly Val Pro Ser Arg Phe Ser
    50                  55                  60

Gly Ser Gly Ser Gly Thr Gln Phe Thr Leu Thr Ile Ser Gly Val Gln
65                  70                  75                  80

Cys Ala Asp Ala Ala Thr Tyr Tyr Cys Gly Gly Tyr Lys Ser Tyr Ser
```

```
                 85                  90                  95
Asn Asp Gly Asn Gly Phe Gly Gly Gly Thr Glu Val Val Val Lys
            100                 105                 110

<210> SEQ ID NO 44
<211> LENGTH: 110
<212> TYPE: PRT
<213> ORGANISM: Oryctolagus cuniculus

<400> SEQUENCE: 44

Leu Val Met Thr Gln Thr Pro Ser Pro Val Ala Ala Val Gly Ser
1               5                   10                  15

Thr Val Ser Ile Ser Cys Gln Ser Ser Glu Ser Val Tyr Ser Asn Trp
            20                  25                  30

Leu Ser Trp Phe Gln Gln Lys Pro Gly Gln Pro Pro Lys Leu Leu Ile
        35                  40                  45

Tyr Arg Ala Ser Asn Leu Glu Thr Gly Val Pro Ser Arg Phe Ser Gly
    50                  55                  60

Ser Gly Ser Gly Thr Gln Phe Thr Leu Thr Ile Ser Gly Val Gln Cys
65                  70                  75                  80

Asp Asp Ala Ala Thr Tyr Tyr Cys Ala Gly Tyr Lys Ser Tyr Tyr Asn
                85                  90                  95

Asp Asp Asn Gly Phe Gly Gly Thr Glu Val Val Val Lys
            100                 105                 110

<210> SEQ ID NO 45
<211> LENGTH: 111
<212> TYPE: PRT
<213> ORGANISM: Oryctolagus cuniculus

<400> SEQUENCE: 45

Gln Val Leu Thr Gln Thr Ala Ser Pro Val Ala Ala Val Gly Gly
1               5                   10                  15

Thr Val Thr Ile Asn Cys Gln Ser Ser Gln Ser Val Phe Ser Asn Ser
            20                  25                  30

Tyr Leu Ser Trp Tyr Gln Gln Lys Pro Gly His Pro Pro Arg Leu Leu
        35                  40                  45

Ile Tyr Asp Ala Ser Thr Leu Ala Ser Gly Val Pro Ser Arg Phe Gly
    50                  55                  60

Gly Ser Gly Ser Gly Thr Gln Phe Thr Leu Thr Ile Gly Gly Val Gln
65                  70                  75                  80

Cys Glu Asp Ala Ala Thr Tyr Tyr Cys Gln Gly Thr Tyr Phe Asp Ala
                85                  90                  95

Ala Trp Tyr Thr Thr Phe Gly Gly Gly Thr Glu Val Val Val Lys
            100                 105                 110

<210> SEQ ID NO 46
<211> LENGTH: 109
<212> TYPE: PRT
<213> ORGANISM: Oryctolagus cuniculus

<400> SEQUENCE: 46

Gln Val Leu Thr Gln Thr Pro Ser Pro Val Ala Ala Val Gly Gly
1               5                   10                  15

Thr Val Thr Ile Ser Cys Gln Ser Ser Gln Ser Val Tyr Asn Asn Asn
            20                  25                  30

Phe Leu Ser Trp Tyr Gln Gln Lys Pro Gly Gln Pro Pro Lys Leu Leu
        35                  40                  45
```

Ile Tyr Gly Ala Ser Thr Leu Ala Ser Gly Val Pro Ser Arg Phe Ser
 50                  55                  60

Gly Ser Gly Ser Gly Thr Gln Phe Thr Leu Thr Ile Ser Glu Asp Gln
 65                  70                  75                  80

Cys Asp Asp Ala Ala Thr Tyr Tyr Cys Gln Gly Tyr Tyr Ser Gly Gly
                 85                  90                  95

Ile Tyr Ser Phe Gly Gly Gly Thr Glu Val Val Val Lys
            100                 105

<210> SEQ ID NO 47
<211> LENGTH: 109
<212> TYPE: PRT
<213> ORGANISM: Oryctolagus cuniculus

<400> SEQUENCE: 47

Leu Val Met Thr Gln Thr Pro Ser Ser Val Ser Ala Ala Val Gly Gly
 1               5                  10                  15

Thr Val Thr Ile Lys Cys Gln Ala Ser Gln Ser Ile Asp Asn Ser Leu
                 20                  25                  30

Thr Trp Tyr Gln Gln Lys Pro Gly Gln Pro Pro Lys Leu Leu Ile Tyr
             35                  40                  45

Arg Ala Ser Thr Leu Glu Ser Gly Val Ser Ser Arg Phe Lys Gly Ser
 50                  55                  60

Gly Ser Gly Thr Glu Phe Thr Leu Thr Ile Ser Asp Leu Glu Cys Ala
 65                  70                  75                  80

Asp Ala Ala Thr Tyr Tyr Cys Gln Gly Tyr Tyr Trp Gly Ser Thr Ala
                 85                  90                  95

Asp Asn Ala Phe Gly Gly Gly Thr Glu Val Val Val Lys
            100                 105

<210> SEQ ID NO 48
<211> LENGTH: 109
<212> TYPE: PRT
<213> ORGANISM: Oryctolagus cuniculus

<400> SEQUENCE: 48

Leu Val Met Thr Gln Thr Pro Ser Ser Val Ser Ala Ala Val Gly Gly
 1               5                  10                  15

Thr Val Thr Ile Lys Cys Gln Ala Ser Gln Ser Ile Asp Ser Ser Leu
                 20                  25                  30

Thr Trp Tyr Gln Gln Lys Pro Gly Gln Pro Pro Lys Leu Leu Ile Tyr
             35                  40                  45

Gly Ala Ser Asn Leu Glu Ser Gly Val Ser Ser Arg Phe Lys Gly Ser
 50                  55                  60

Gly Ser Gly Thr Glu Phe Thr Leu Thr Ile Ser Asp Leu Glu Cys Ala
 65                  70                  75                  80

Asp Ala Ala Thr Tyr Tyr Cys Gln Gly Tyr Tyr Trp Gly Ser Ala Ala
                 85                  90                  95

Asp Asn Ala Phe Gly Gly Gly Thr Glu Val Val Val Lys
            100                 105

<210> SEQ ID NO 49
<211> LENGTH: 111
<212> TYPE: PRT
<213> ORGANISM: Oryctolagus cuniculus

<400> SEQUENCE: 49

Tyr Asp Met Thr Gln Thr Pro Ala Ser Val Glu Ala Ala Val Gly Gly
 1               5                  10                  15

```
Thr Val Thr Ile Lys Cys Gln Ala Ser Gln Ser Ile Ser Ile Tyr Leu
            20                  25                  30

Ala Trp Tyr Gln Gln Lys Pro Gly Gln Pro Lys Leu Leu Ile Tyr
        35                  40                  45

Lys Ala Ser Thr Leu Ala Ser Gly Val Pro Ser Arg Phe Lys Gly Ser
 50                  55                  60

Gly Ser Gly Thr Glu Phe Thr Leu Thr Ile Ser Asp Leu Glu Cys Ala
 65                  70                  75                  80

Asp Ala Ala Thr Tyr Tyr Cys Gln Ser Tyr Tyr Gly Ser Ser Ser Asp
                85                  90                  95

Thr Ser Tyr Asn Val Phe Gly Gly Gly Thr Glu Val Val Val Lys
            100                 105                 110

<210> SEQ ID NO 50
<211> LENGTH: 109
<212> TYPE: PRT
<213> ORGANISM: Oryctolagus cuniculus

<400> SEQUENCE: 50

Tyr Asp Met Thr Gln Thr Pro Ala Ser Val Glu Ala Val Gly Gly
 1               5                  10                  15

Thr Val Thr Ile Lys Cys Gln Ala Ser Glu Asn Ile Gly Asn Ala Leu
            20                  25                  30

Ala Trp Tyr Gln Gln Lys Pro Gly Gln Pro Pro Lys Leu Leu Ile Tyr
        35                  40                  45

Arg Ala Ser Thr Leu Glu Ser Gly Val Pro Ser Arg Phe Lys Gly Ser
 50                  55                  60

Ala Ser Gly Thr Glu Phe Thr Leu Thr Ile Ser Asp Leu Glu Cys Ala
 65                  70                  75                  80

Asp Ala Ala Thr Tyr Tyr Cys Gln Gln Gly Tyr Ser Phe Gly Gly Val
                85                  90                  95

Asp Asn Thr Phe Gly Gly Gly Thr Glu Val Val Val Lys
            100                 105

<210> SEQ ID NO 51
<211> LENGTH: 109
<212> TYPE: PRT
<213> ORGANISM: Oryctolagus cuniculus

<400> SEQUENCE: 51

Leu Val Met Thr Gln Thr Pro Ala Ser Val Glu Val Ala Val Gly Gly
 1               5                  10                  15

Thr Val Thr Ile Asn Cys Gln Ala Ser Gln Ser Ile Gly Ser Ser Leu
            20                  25                  30

Ala Trp Tyr Gln Gln Lys Pro Gly Gln Pro Lys Leu Leu Ile Tyr
        35                  40                  45

Arg Ala Ser Thr Leu Ala Ser Gly Val Pro Ser Arg Phe Ser Gly Ser
 50                  55                  60

Gly Ser Gly Thr Glu Phe Thr Leu Thr Ile Ser Asp Leu Glu Cys Ala
 65                  70                  75                  80

Asp Ala Ala Thr Tyr Tyr Cys Gln Gly Tyr Tyr Tyr Ser Asp Ser Ala
                85                  90                  95

Glu Asn Ala Phe Gly Gly Gly Thr Glu Val Val Val Lys
            100                 105

<210> SEQ ID NO 52
<211> LENGTH: 111
```

<212> TYPE: PRT
<213> ORGANISM: Oryctolagus cuniculus

<400> SEQUENCE: 52

Asp Ile Val Met Thr Gln Thr Pro Ala Ser Val Glu Ala Ala Val Gly
1               5                   10                  15

Gly Thr Val Thr Ile Lys Cys Gln Ala Ser Glu Thr Ile Asn Thr Phe
            20                  25                  30

Leu Ser Trp Tyr Gln Gln Lys Pro Gly Gln Pro Pro Lys Leu Leu Ile
        35                  40                  45

Tyr Gln Ala Ser Thr Leu Ala Ser Gly Val Pro Ser Arg Phe Lys Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Gln Ser Tyr Phe Tyr Gly Ser Gly
                85                  90                  95

Asn Tyr Gly Phe Val Phe Gly Gly Thr Glu Val Val Val Arg
            100                 105                 110

<210> SEQ ID NO 53
<211> LENGTH: 111
<212> TYPE: PRT
<213> ORGANISM: Oryctolagus cuniculus

<400> SEQUENCE: 53

Asp Ile Val Met Thr Gln Thr Pro Ala Ser Val Glu Ala Ala Val Gly
1               5                   10                  15

Gly Thr Val Thr Ile Lys Cys Gln Ala Ser Glu Ser Ile Asn Ser Trp
            20                  25                  30

Leu Ser Trp Tyr Gln Gln Lys Ser Gly Gln Pro Pro Lys Leu Leu Ile
        35                  40                  45

Tyr Gln Ala Ser Thr Leu Ala Ser Gly Val Pro Ser Arg Phe Lys Gly
    50                  55                  60

Ser Gly Ser Gly Thr Gln Phe Thr Leu Thr Ile Ser Asp Leu Glu Cys
65                  70                  75                  80

Val Asp Ala Ala Thr Tyr Tyr Cys Gln Ser Tyr Phe Tyr Lys Ser Gly
                85                  90                  95

Ser Tyr Gly Phe Ile Phe Gly Ala Gly Thr Glu Val Val Val Arg
            100                 105                 110

<210> SEQ ID NO 54
<211> LENGTH: 109
<212> TYPE: PRT
<213> ORGANISM: Oryctolagus cuniculus

<400> SEQUENCE: 54

Ile Glu Met Thr Gln Thr Pro Phe Ser Val Ser Ala Ala Val Gly Gly
1               5                   10                  15

Thr Val Thr Ile Asn Cys Gln Ala Ser Glu Ser Ile Tyr Ser Asn Leu
            20                  25                  30

Ala Trp Tyr Gln Gln Lys Pro Gly Gln Pro Pro Lys Leu Leu Ile Tyr
        35                  40                  45

Ala Ala Ser Tyr Leu Ala Ser Gly Val Pro Ser Arg Phe Lys Gly Ser
    50                  55                  60

Gly Ser Gly Thr Glu Tyr Thr Leu Thr Ile Ser Gly Val Gln Cys Ala
65                  70                  75                  80

Asp Ala Ala Thr Tyr Tyr Cys Gln Ser Ala His Tyr Ser Ser Ser Gly
                85                  90                  95

Asp Ile Ala Phe Gly Gly Gly Thr Glu Val Val Val Lys
            100                 105

<210> SEQ ID NO 55
<211> LENGTH: 109
<212> TYPE: PRT
<213> ORGANISM: Oryctolagus cuniculus

<400> SEQUENCE: 55

Ile Glu Met Thr Gln Thr Pro Phe Ser Val Ser Ala Ala Val Gly Gly
1               5                   10                  15

Thr Val Thr Ile Asn Cys Gln Ala Ser Glu Ser Ile Tyr Ser Asn Leu
            20                  25                  30

Ala Trp Tyr Gln Gln Lys Pro Gly Gln Pro Pro Lys Leu Leu Ile Tyr
        35                  40                  45

Ala Ala Ser Tyr Leu Ala Ser Gly Val Pro Ser Arg Phe Lys Gly Ser
    50                  55                  60

Gly Ser Gly Thr Glu Tyr Thr Leu Thr Ile Ser Gly Val Gln Cys Ala
65                  70                  75                  80

Asp Ala Ala Thr Tyr Tyr Cys Gln Ser Ala His Tyr Ser Ser Ser Gly
                85                  90                  95

Asp Ile Ala Phe Gly Gly Gly Thr Glu Val Val Val Lys
            100                 105

<210> SEQ ID NO 56
<211> LENGTH: 109
<212> TYPE: PRT
<213> ORGANISM: Oryctolagus cuniculus

<400> SEQUENCE: 56

Ile Glu Met Thr Gln Thr Pro Phe Ser Val Ser Ala Ala Val Gly Gly
1               5                   10                  15

Thr Val Thr Ile Asn Cys Gln Ala Ser Glu Ser Ile Tyr Ser Asn Leu
            20                  25                  30

Ala Trp Tyr Gln Gln Lys Pro Gly Gln Pro Pro Lys Leu Leu Ile Tyr
        35                  40                  45

Ala Ala Phe Tyr Leu Ala Ser Gly Val Pro Ser Arg Phe Lys Gly Ser
    50                  55                  60

Gly Ser Gly Thr Glu Tyr Thr Leu Thr Ile Ser Gly Val Gln Cys Ala
65                  70                  75                  80

Asp Ala Gly Thr Tyr Tyr Cys Gln Ser Ala Asn Tyr Ser Ser Ser Gly
                85                  90                  95

Asp Ile Ala Phe Gly Gly Gly Thr Glu Val Val Val Lys
            100                 105

<210> SEQ ID NO 57
<211> LENGTH: 110
<212> TYPE: PRT
<213> ORGANISM: Oryctolagus cuniculus

<400> SEQUENCE: 57

Asp Ile Val Met Thr Gln Thr Pro Ala Ser Val Ser Glu Pro Val Gly
1               5                   10                  15

Gly Thr Val Thr Ile Lys Cys Gln Ala Ser Gln Ser Ile Arg Ser Trp
            20                  25                  30

Leu Ala Trp Tyr Gln Gln Lys Pro Gly Gln Pro Pro Lys Leu Leu Ile
        35                  40                  45

Tyr Glu Ala Ser Lys Leu Ala Phe Gly Val Pro Ser Arg Phe Ser Gly

```
                50                  55                  60
Ser Gly Tyr Gly Thr Gln Phe Thr Leu Thr Ile Ser Gly Val Gln Cys
 65                  70                  75                  80

Asp Asp Ala Ala Thr Tyr Tyr Cys Gln Asn Ser Tyr Gly Trp Thr Ser
                 85                  90                  95

Tyr Gly Ala Thr Phe Gly Gly Gly Thr Glu Val Val Val Lys
            100                 105                 110

<210> SEQ ID NO 58
<211> LENGTH: 110
<212> TYPE: PRT
<213> ORGANISM: Oryctolagus cuniculus

<400> SEQUENCE: 58

Asp Ile Val Met Thr Gln Thr Pro Ala Ser Val Ser Glu Pro Val Gly
 1               5                  10                  15

Gly Thr Val Thr Ile Lys Cys Gln Ala Ser Gln Ser Ile Arg Ser Trp
                20                  25                  30

Leu Ala Trp Tyr Gln Gln Lys Pro Gly Gln Pro Pro Lys Leu Leu Ile
            35                  40                  45

Tyr Glu Ala Ser Lys Leu Ala Phe Gly Val Pro Ser Arg Phe Ser Gly
 50                  55                  60

Ser Gly Tyr Gly Thr Gln Phe Thr Leu Thr Ile Ser Gly Val Gln Cys
 65                  70                  75                  80

Asp Asp Ala Ala Thr Tyr Tyr Cys Gln Asn Asp Tyr Gly Trp Thr Ser
                 85                  90                  95

Tyr Gly Ala Thr Phe Gly Gly Gly Thr Glu Val Val Val Lys
            100                 105                 110

<210> SEQ ID NO 59
<211> LENGTH: 110
<212> TYPE: PRT
<213> ORGANISM: Oryctolagus cuniculus

<400> SEQUENCE: 59

Asp Val Val Met Thr Gln Thr Pro Ser Ser Ala Ser Glu Pro Val Gly
 1               5                  10                  15

Gly Thr Val Thr Ile Lys Cys Gln Ala Ser Glu Asn Ile Arg Ser Trp
                20                  25                  30

Leu Ala Trp Tyr Gln Gln Lys Pro Gly Gln Pro Pro Lys Leu Leu Ile
            35                  40                  45

Tyr Gln Ala Ser Lys Leu Ala Ser Gly Val Pro Ser Arg Phe Lys Gly
 50                  55                  60

Ser Gly Tyr Gly Thr Glu Phe Thr Leu Thr Ile Ser Asp Leu Glu Cys
 65                  70                  75                  80

Ala Asp Val Gly Thr Tyr Tyr Cys Gln Asn Cys Tyr Ser Phe Ser Thr
                 85                  90                  95

Tyr Gly Ala Ala Phe Gly Gly Gly Thr Glu Val Val Val Arg
            100                 105                 110

<210> SEQ ID NO 60
<211> LENGTH: 110
<212> TYPE: PRT
<213> ORGANISM: Oryctolagus cuniculus

<400> SEQUENCE: 60

Asp Val Val Met Thr Gln Thr Pro Ser Ser Ala Ser Glu Pro Val Gly
 1               5                  10                  15
```

```
Gly Thr Val Thr Ile Lys Cys Gln Ala Ser Glu Ser Ile Arg Ser Trp
            20                  25                  30

Leu Ala Trp Tyr Gln Lys Pro Gly Gln Pro Pro Lys Leu Leu Ile
        35                  40                  45

Tyr Gln Ala Ser Lys Leu Ala Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Gly Thr Tyr Tyr Cys Gln Asn Cys Tyr Ser Phe Ser Ala
                85                  90                  95

Tyr Gly Ala Ala Phe Gly Gly Thr Glu Val Val Val Lys
            100                 105                 110
```

<210> SEQ ID NO 61
<211> LENGTH: 110
<212> TYPE: PRT
<213> ORGANISM: Oryctolagus cuniculus

<400> SEQUENCE: 61

```
Asp Val Val Met Thr Gln Thr Pro Ser Ser Ala Ser Glu Pro Val Gly
1               5                   10                  15

Gly Thr Val Thr Ile Lys Cys Gln Ala Ser Glu Ser Ile Arg Asn Trp
            20                  25                  30

Leu Ala Trp Tyr His Gln Lys Pro Gly Gln Pro Pro Lys Leu Leu Ile
        35                  40                  45

Tyr Gln Ala Ser Ser Leu Ala Ser Gly Val Pro Ser Arg Phe Lys Gly
    50                  55                  60

Ser Gly Ala Gly Thr Asp Tyr Thr Leu Thr Ile Ser Asp Leu Glu Cys
65                  70                  75                  80

Ala Asp Ala Gly Thr Tyr Tyr Cys Gln Asn Cys Tyr Ser Phe Ser Ser
                85                  90                  95

Tyr Gly Ala Ala Phe Gly Gly Thr Glu Val Val Val Arg
            100                 105                 110
```

<210> SEQ ID NO 62
<211> LENGTH: 110
<212> TYPE: PRT
<213> ORGANISM: Oryctolagus cuniculus

<400> SEQUENCE: 62

```
Asp Val Val Met Thr Gln Thr Pro Ser Ser Ala Ser Glu Pro Val Gly
1               5                   10                  15

Gly Thr Val Thr Ile Lys Cys Gln Ala Ser Glu Ser Ile Ser Asn Trp
            20                  25                  30

Leu Ala Trp Tyr Gln Gln Lys Pro Gly Gln Pro Pro Lys Leu Leu Ile
        35                  40                  45

Tyr Gln Ala Ser Arg Leu Ala Ser Gly Val Pro Ser Arg Phe Lys Gly
    50                  55                  60

Ser Gly Ser Gly Thr Glu Tyr Thr Leu Thr Ile Ser Asp Leu Glu Cys
65                  70                  75                  80

Ala Asp Ala Gly Thr Tyr Tyr Cys Gln Asn Ser Tyr Arg Phe Ser Ile
                85                  90                  95

Tyr Gly Gly Ala Phe Gly Gly Gly Thr Glu Val Val Val Arg
            100                 105                 110
```

<210> SEQ ID NO 63
<211> LENGTH: 110
<212> TYPE: PRT

<213> ORGANISM: Oryctolagus cuniculus

<400> SEQUENCE: 63

Asp Val Val Met Thr Gln Thr Pro Ala Ser Val Ser Ala Ala Val Gly
1               5                   10                  15

Gly Thr Val Thr Ile Lys Cys Gln Ala Ser Gln Ser Ile Asn Thr Trp
            20                  25                  30

Leu Ser Trp Tyr Gln Gln Lys Pro Gly Gln Pro Pro Lys Leu Leu Ile
        35                  40                  45

Tyr Gln Ala Ser Lys Leu Ala Ser Gly Val Pro Ser Arg Phe Ser Val
50                  55                  60

Ser Gly Tyr Gly Thr Glu Phe Thr Leu Thr Ile Ser Asp Leu Glu Cys
65                  70                  75                  80

Ala Asp Ala Ala Thr Tyr Tyr Cys Gln Asn Asn Tyr Leu Met Ala Thr
                85                  90                  95

Tyr Gly Gly Pro Phe Gly Gly Gly Thr Glu Val Val Val Lys
            100                 105                 110

<210> SEQ ID NO 64
<211> LENGTH: 110
<212> TYPE: PRT
<213> ORGANISM: Oryctolagus cuniculus

<400> SEQUENCE: 64

Asp Val Val Met Thr Gln Thr Pro Ala Ser Val Ser Ala Ala Val Gly
1               5                   10                  15

Gly Thr Val Thr Ile Lys Cys Gln Ala Ser Gln Ser Ile Asn Thr Trp
            20                  25                  30

Leu Ser Trp Tyr Gln Gln Lys Pro Gly Gln Pro Pro Lys Leu Leu Ile
        35                  40                  45

Tyr Gln Ala Ser Lys Leu Ala Ser Gly Val Pro Ser Arg Phe Ser Val
50                  55                  60

Ser Gly Tyr Gly Thr Glu Phe Thr Leu Thr Ile Ser Asp Leu Glu Cys
65                  70                  75                  80

Ala Asp Ala Ala Thr Tyr Tyr Cys Gln Asn Asn Tyr Leu Met Ala Thr
                85                  90                  95

Tyr Gly Gly Pro Phe Gly Gly Gly Thr Glu Val Val Val Lys
            100                 105                 110

<210> SEQ ID NO 65
<211> LENGTH: 110
<212> TYPE: PRT
<213> ORGANISM: Oryctolagus cuniculus

<400> SEQUENCE: 65

Asp Val Val Met Thr Gln Thr Pro Ala Ser Val Ser Ala Ala Val Gly
1               5                   10                  15

Gly Thr Val Thr Ile Lys Cys Gln Ala Ser Gln Ser Ile Asn Thr Trp
            20                  25                  30

Leu Ser Trp Tyr Gln Gln Lys Pro Gly Gln Pro Pro Lys Leu Leu Ile
        35                  40                  45

Tyr Gln Ala Ser Lys Leu Ala Ser Gly Val Pro Ser Arg Phe Ser Val
50                  55                  60

Ser Gly Tyr Gly Thr Glu Phe Thr Leu Thr Ile Ser Asp Leu Glu Cys
65                  70                  75                  80

Ala Asp Ala Ala Thr Tyr Tyr Cys Gln Asn Asn Tyr Leu Met Ala Thr
                85                  90                  95

```
Tyr Gly Gly Pro Phe Gly Gly Gly Thr Glu Val Val Val Lys
            100                 105                 110

<210> SEQ ID NO 66
<211> LENGTH: 110
<212> TYPE: PRT
<213> ORGANISM: Oryctolagus cuniculus

<400> SEQUENCE: 66

Asp Val Val Met Thr Gln Thr Pro Ala Ser Val Ser Ala Ala Val Gly
1               5                   10                  15

Gly Thr Val Thr Ile Lys Cys Gln Ala Ser Gln Ser Ile Ser Ser Trp
            20                  25                  30

Leu Ser Trp Tyr His Gln Lys Pro Gly Gln Pro Pro Lys Leu Leu Ile
        35                  40                  45

Tyr Gln Ala Ser Lys Leu Ala Ser Gly Val Pro Ser Arg Phe Ser Gly
    50                  55                  60

Ser Gly Tyr Gly Thr Glu Phe Thr Leu Thr Ile Ser Asp Leu Glu Cys
65                  70                  75                  80

Ala Asp Ala Ala Thr Tyr Tyr Cys Gln Asn Asn Tyr Leu Met Ala Thr
                85                  90                  95

Tyr Gly Gly Pro Phe Gly Gly Gly Thr Glu Val Val Val Lys
            100                 105                 110

<210> SEQ ID NO 67
<211> LENGTH: 110
<212> TYPE: PRT
<213> ORGANISM: Oryctolagus cuniculus

<400> SEQUENCE: 67

Asp Val Val Met Thr Gln Thr Pro Ala Ser Val Ser Glu Pro Val Gly
1               5                   10                  15

Gly Thr Val Thr Ile Lys Cys Gln Ala Ser Gln Ser Ile Ser Gly Trp
            20                  25                  30

Leu Ser Trp Tyr Gln Gln Lys Pro Gly Gln Pro Pro Lys Leu Leu Ile
        35                  40                  45

Tyr Gln Ala Ser Lys Leu Ala Ser Gly Val Pro Ser Arg Phe Lys Gly
    50                  55                  60

Ser Gly Ser Gly Thr Glu Tyr Thr Leu Thr Ile Ser Asp Leu Glu Cys
65                  70                  75                  80

Ala Asp Ala Ala Thr Tyr Tyr Cys Gln Ser Val Tyr Leu Ile Ser Thr
                85                  90                  95

Tyr Gly Ala Thr Phe Gly Gly Gly Thr Glu Val Val Val Lys
            100                 105                 110

<210> SEQ ID NO 68
<211> LENGTH: 110
<212> TYPE: PRT
<213> ORGANISM: Oryctolagus cuniculus

<400> SEQUENCE: 68

Asp Val Val Met Thr Gln Thr Pro Ala Ser Val Ser Glu Pro Val Gly
1               5                   10                  15

Gly Thr Val Thr Ile Lys Cys Gln Ala Ser Gln Ser Ile Ser Gly Trp
            20                  25                  30

Leu Ser Trp Tyr Gln Gln Lys Pro Gly Gln Pro Pro Lys Leu Leu Ile
        35                  40                  45

Tyr Gln Ala Ser Lys Leu Ala Ser Gly Val Pro Ser Arg Phe Lys Gly
    50                  55                  60
```

```
Ser Gly Ser Gly Thr Glu Tyr Thr Leu Thr Ile Ser Asp Leu Glu Cys
 65                  70                  75                  80

Ala Asp Ala Ala Thr Tyr Tyr Cys Gln Ser Val Tyr Leu Ile Ser Thr
                 85                  90                  95

Tyr Gly Ala Thr Phe Gly Gly Gly Thr Glu Val Val Val Lys
            100                 105                 110

<210> SEQ ID NO 69
<211> LENGTH: 110
<212> TYPE: PRT
<213> ORGANISM: Oryctolagus cuniculus

<400> SEQUENCE: 69

Asp Val Val Met Thr Gln Thr Pro Ala Ser Val Ser Glu Pro Val Gly
 1               5                  10                  15

Gly Thr Val Thr Ile Lys Cys Gln Ala Ser Gln Ser Ile Ser Gly Trp
                20                  25                  30

Leu Ser Trp Tyr Gln Gln Lys Pro Gly Gln Pro Pro Lys Leu Leu Ile
             35                  40                  45

Tyr Gln Ala Ser Lys Leu Ala Ser Gly Val Pro Ser Arg Phe Lys Gly
     50                  55                  60

Ser Gly Ser Gly Thr Glu Tyr Thr Leu Thr Ile Ser Asp Leu Glu Cys
 65                  70                  75                  80

Ala Asp Ala Ala Thr Tyr Tyr Cys Gln Ser Val Tyr Leu Val Ser Thr
                 85                  90                  95

Tyr Gly Ala Thr Phe Gly Gly Gly Thr Glu Val Val Val Lys
            100                 105                 110

<210> SEQ ID NO 70
<211> LENGTH: 110
<212> TYPE: PRT
<213> ORGANISM: Oryctolagus cuniculus

<400> SEQUENCE: 70

Asp Val Val Met Thr Gln Thr Pro Ser Ser Val Ser Glu Pro Val Gly
 1               5                  10                  15

Gly Thr Val Thr Ile Lys Cys Gln Ala Ser Gln Ser Ile Asn Ser Trp
                20                  25                  30

Leu Ser Trp Phe Gln Gln Lys Pro Gly Gln Arg Pro Lys Leu Leu Ile
             35                  40                  45

Trp His Ala Ser Thr Leu Ala Ser Gly Val Pro Ser Arg Phe Ser Gly
     50                  55                  60

Ser Gly Ser Gly Thr Glu Tyr Thr Leu Thr Ile Ser Asp Leu Glu Cys
 65                  70                  75                  80

Ala Asp Ala Ala Thr Tyr Tyr Cys Glu Asn Asn Arg Asn Met Asp Ser
                 85                  90                  95

Val Gly Ala Ala Phe Gly Gly Gly Thr Glu Val Val Val Lys
            100                 105                 110

<210> SEQ ID NO 71
<211> LENGTH: 109
<212> TYPE: PRT
<213> ORGANISM: Oryctolagus cuniculus

<400> SEQUENCE: 71

Gln Val Leu Thr Gln Thr Pro Ala Ser Val Ser Ala Ala Val Gly Gly
 1               5                  10                  15

Thr Val Thr Ile Ser Cys Gln Ser Ser Gln Asn Val Tyr Ser Asn Asp
```

```
            20                  25                  30
Leu Leu Ser Trp Tyr Gln Gln Lys Leu Gly Gln Pro Pro Lys Leu Leu
        35                  40                  45

Ile Tyr Glu Ala Ser Lys Leu Ala Ser Gly Val Pro Pro Arg Phe Ser
    50                  55                  60

Gly Ser Gly Ser Gly Thr Gln Phe Thr Leu Thr Ile Ser Gly Val Gln
65                  70                  75                  80

Cys Asp Asp Ala Ala Thr Tyr Tyr Cys Ala Gly Ala Tyr Ser Gly Asn
                85                  90                  95

Ile Asn Val Phe Gly Gly Gly Ala Glu Val Val Val Lys
            100                 105

<210> SEQ ID NO 72
<211> LENGTH: 109
<212> TYPE: PRT
<213> ORGANISM: Oryctolagus cuniculus

<400> SEQUENCE: 72

Gln Val Leu Thr Gln Thr Pro Ala Ser Val Ser Ala Ala Val Gly Gly
1               5                   10                  15

Thr Val Thr Ile Ser Cys Gln Ser Ser Gln Asn Val Tyr Ser Asn Asp
            20                  25                  30

Leu Leu Ser Trp Tyr Gln Gln Lys Leu Gly Gln Pro Pro Lys Leu Leu
        35                  40                  45

Ile Tyr Glu Ala Ser Lys Leu Ala Ser Gly Val Pro Pro Arg Phe Ser
    50                  55                  60

Gly Ser Gly Ser Gly Thr Gln Phe Thr Leu Thr Ile Ser Gly Val Gln
65                  70                  75                  80

Cys Asp Asp Ala Ala Thr Tyr Tyr Cys Ala Gly Ala Tyr Ser Gly Asn
                85                  90                  95

Ile Asn Val Phe Gly Gly Gly Ala Glu Val Val Val Lys
            100                 105

<210> SEQ ID NO 73
<211> LENGTH: 109
<212> TYPE: PRT
<213> ORGANISM: Oryctolagus cuniculus

<400> SEQUENCE: 73

Gln Val Leu Thr Gln Thr Pro Ser Ser Val Ser Ala Ala Val Gly Gly
1               5                   10                  15

Thr Val Thr Ile Ser Cys Gln Ser Ser Glu Ser Val Tyr Ser Asn Asn
            20                  25                  30

Arg Leu Ser Trp Tyr Gln Gln Lys Pro Gly Gln Pro Pro Lys Gln Leu
        35                  40                  45

Ile Tyr Phe Ala Ser Thr Leu Ala Ser Gly Val Pro Ser Arg Phe Lys
    50                  55                  60

Gly Ser Gly Ser Gly Thr Gln Phe Thr Leu Thr Ile Ser Asp Leu Glu
65                  70                  75                  80

Cys Asp Asp Ala Ala Thr Tyr Tyr Cys Ala Gly Gly Tyr Ser Gly Val
                85                  90                  95

Ile Tyr Val Phe Gly Gly Gly Thr Glu Val Val Val Lys
            100                 105

<210> SEQ ID NO 74
<211> LENGTH: 112
<212> TYPE: PRT
<213> ORGANISM: Oryctolagus cuniculus
```

<400> SEQUENCE: 74

Leu Val Met Thr Gln Thr Pro Ala Ser Val Ser Ala Ala Val Gly Gly
1               5                   10                  15

Thr Val Thr Ile Asn Cys Gln Ala Ser Gln Ser Val Tyr Gly Asp Asn
            20                  25                  30

Glu Leu Ser Trp Tyr Gln Gln Lys Ser Gly Gln Pro Pro Lys Leu Leu
        35                  40                  45

Ile Tyr Lys Ala Ser Thr Leu Ala Ser Gly Val Pro Ser Arg Phe Lys
50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Leu Gly Gly Tyr Asp Cys Ser
                85                  90                  95

Gly Val Asp Cys Phe Val Phe Gly Gly Gly Thr Glu Val Val Val Lys
            100                 105                 110

<210> SEQ ID NO 75
<211> LENGTH: 110
<212> TYPE: PRT
<213> ORGANISM: Oryctolagus cuniculus

<400> SEQUENCE: 75

Val Leu Thr Gln Thr Pro Ser Pro Val Ser Ala Ala Val Gly Gly Thr
1               5                   10                  15

Val Thr Ile Ser Cys Gln Ala Ser Gln Ser Val Tyr Asn Asp Asn Trp
            20                  25                  30

Leu Ala Trp Tyr Gln Gln Lys Pro Gly Gln Pro Pro Lys Leu Leu Ile
        35                  40                  45

Tyr Asp Thr Ser Lys Leu Ala Ser Gly Val Pro Ser Arg Phe Lys Ala
50                  55                  60

Ser Gly Ser Gly Thr Gln Phe Thr Leu Thr Ile Ser Gly Ala Gln Cys
65                  70                  75                  80

Asp Asp Ala Ala Thr Tyr Tyr Cys Gln Gly Thr Tyr Phe Ser Ser Ala
                85                  90                  95

Trp Phe Asn Ala Phe Gly Gly Gly Thr Glu Val Val Val Lys
            100                 105                 110

<210> SEQ ID NO 76
<211> LENGTH: 111
<212> TYPE: PRT
<213> ORGANISM: Oryctolagus cuniculus

<400> SEQUENCE: 76

Ile Val Met Thr Gln Thr Pro Ser Ser Lys Ser Val Pro Val Gly Asp
1               5                   10                  15

Thr Val Thr Ile Asn Cys Gln Ala Ser Glu Ser Val Tyr Ser Asn Asn
            20                  25                  30

Arg Leu Ala Trp Phe Gln Gln Lys Pro Gly Gln Pro Pro Lys Leu Leu
        35                  40                  45

Ile Tyr Tyr Ala Ser Thr Leu Ala Ser Gly Val Pro Ser Arg Phe Lys
50                  55                  60

Gly Ser Gly Ser Gly Thr Gln Phe Thr Leu Thr Ile Ser Asp Val Val
65                  70                  75                  80

Cys Asp Asp Ala Ala Thr Tyr Tyr Cys Ala Gly Tyr Arg Ser Ser Thr
                85                  90                  95

Thr Asp Gly Thr Ala Phe Gly Gly Gly Thr Glu Val Val Val Lys

<210> SEQ ID NO 77
<211> LENGTH: 6
<212> TYPE: PRT
<213> ORGANISM: Oryctolagus cuniculus
<220> FEATURE:
<221> NAME/KEY: VARIANT
<222> LOCATION: 3
<223> OTHER INFORMATION: Xaa is Ala or Asp

<400> SEQUENCE: 77

Asn Asn Xaa Val Met Cys
1               5

<210> SEQ ID NO 78
<211> LENGTH: 17
<212> TYPE: PRT
<213> ORGANISM: Oryctolagus cuniculus
<220> FEATURE:
<221> NAME/KEY: VARIANT
<222> LOCATION: 10
<223> OTHER INFORMATION: Xaa is Glu or Ala

<400> SEQUENCE: 78

Cys Ile Met Thr Thr Asp Val Val Thr Xaa Tyr Ala Asn Trp Ala Lys
1               5                   10                  15

Ser

<210> SEQ ID NO 79
<211> LENGTH: 12
<212> TYPE: PRT
<213> ORGANISM: Oryctolagus cuniculus

<400> SEQUENCE: 79

Asp Ser Val Gly Ser Pro Leu Met Ser Phe Asp Leu
1               5                   10

<210> SEQ ID NO 80
<211> LENGTH: 13
<212> TYPE: PRT
<213> ORGANISM: Oryctolagus cuniculus
<220> FEATURE:
<221> NAME/KEY: VARIANT
<222> LOCATION: 5
<223> OTHER INFORMATION: Xaa is Asn or Ser
<220> FEATURE:
<221> NAME/KEY: VARIANT
<222> LOCATION: 6
<223> OTHER INFORMATION: Xaa is Leu or Val
<220> FEATURE:
<221> NAME/KEY: VARIANT
<222> LOCATION: 8
<223> OTHER INFORMATION: Xaa is Asn or Gly

<400> SEQUENCE: 80

Gln Ala Ser Gln Xaa Xaa Tyr Xaa Asn Asn Glu Leu Ser
1               5                   10

<210> SEQ ID NO 81
<211> LENGTH: 7
<212> TYPE: PRT
<213> ORGANISM: Oryctolagus cuniculus
<220> FEATURE:
<221> NAME/KEY: VARIANT
<222> LOCATION: 1
<223> OTHER INFORMATION: Xaa is Trp or Arg

<400> SEQUENCE: 81

```
Xaa Ala Ser Thr Leu Ala Ser
1               5

<210> SEQ ID NO 82
<211> LENGTH: 12
<212> TYPE: PRT
<213> ORGANISM: Oryctolagus cuniculus
<220> FEATURE:
<221> NAME/KEY: VARIANT
<222> LOCATION: 1
<223> OTHER INFORMATION: Xaa is Ala, Ser, or Gly
<220> FEATURE:
<221> NAME/KEY: VARIANT
<222> LOCATION: 7
<223> OTHER INFORMATION: Xaa is Ser or Tyr
<220> FEATURE:
<221> NAME/KEY: VARIANT
<222> LOCATION: 9
<223> OTHER INFORMATION: Xaa is Asp or Gly
<220> FEATURE:
<221> NAME/KEY: VARIANT
<222> LOCATION: 11
<223> OTHER INFORMATION: Xaa is Asn or Ser

<400> SEQUENCE: 82

Xaa Gly Tyr Lys Ser Tyr Xaa Asn Xaa Gly Xaa Gly
1               5                   10

<210> SEQ ID NO 83
<211> LENGTH: 6
<212> TYPE: PRT
<213> ORGANISM: Oryctolagus cuniculus
<220> FEATURE:
<221> NAME/KEY: VARIANT
<222> LOCATION: 2
<223> OTHER INFORMATION: Xaa is Ser, Asn, or Gly
<220> FEATURE:
<221> NAME/KEY: VARIANT
<222> LOCATION: 4
<223> OTHER INFORMATION: Xaa is Tyr or Asp

<400> SEQUENCE: 83

Ser Xaa Tyr Xaa Met Cys
1               5

<210> SEQ ID NO 84
<211> LENGTH: 17
<212> TYPE: PRT
<213> ORGANISM: Oryctolagus cuniculus
<220> FEATURE:
<221> NAME/KEY: VARIANT
<222> LOCATION: 7
<223> OTHER INFORMATION: Xaa is Asn or Gly
<220> FEATURE:
<221> NAME/KEY: VARIANT
<222> LOCATION: 8
<223> OTHER INFORMATION: Xaa is Asn or Arg
<220> FEATURE:
<221> NAME/KEY: VARIANT
<222> LOCATION: 10
<223> OTHER INFORMATION: Xaa is Tyr or His
<220> FEATURE:
<221> NAME/KEY: VARIANT
<222> LOCATION: 13
<223> OTHER INFORMATION: Xaa is Tyr or Ser
<220> FEATURE:
<221> NAME/KEY: VARIANT
<222> LOCATION: 15
<223> OTHER INFORMATION: Xaa is Gly or Ala

<400> SEQUENCE: 84

Cys Ile Tyr Thr Gly Ser Xaa Xaa Thr Xaa Tyr Ala Xaa Trp Xaa Lys
1               5                   10                  15
```

Gly

<210> SEQ ID NO 85
<211> LENGTH: 9
<212> TYPE: PRT
<213> ORGANISM: Oryctolagus cuniculus
<220> FEATURE:
<221> NAME/KEY: VARIANT
<222> LOCATION: 1
<223> OTHER INFORMATION: Xaa is Ala or Gly
<220> FEATURE:
<221> NAME/KEY: VARIANT
<222> LOCATION: 2
<223> OTHER INFORMATION: Xaa is Ile or Asn
<220> FEATURE:
<221> NAME/KEY: VARIANT
<222> LOCATION: 8
<223> OTHER INFORMATION: Xaa is Val, Ala, or Gly
<220> FEATURE:
<221> NAME/KEY: VARIANT
<222> LOCATION: 9
<223> OTHER INFORMATION: Xaa is Leu or Val

<400> SEQUENCE: 85

Xaa Xaa Ser Ile Asn Val Tyr Xaa Xaa
1               5

<210> SEQ ID NO 86
<211> LENGTH: 11
<212> TYPE: PRT
<213> ORGANISM: Oryctolagus cuniculus
<220> FEATURE:
<221> NAME/KEY: VARIANT
<222> LOCATION: 7
<223> OTHER INFORMATION: Xaa is Asp or Gly
<220> FEATURE:
<221> NAME/KEY: VARIANT
<222> LOCATION: 8
<223> OTHER INFORMATION: Xaa is Asn or Ser
<220> FEATURE:
<221> NAME/KEY: VARIANT
<222> LOCATION: 11
<223> OTHER INFORMATION: Xaa is Thr or Ala

<400> SEQUENCE: 86

Gln Ala Ser Gln Ser Ile Xaa Xaa Ser Leu Xaa
1               5                   10

<210> SEQ ID NO 87
<211> LENGTH: 7
<212> TYPE: PRT
<213> ORGANISM: Oryctolagus cuniculus
<220> FEATURE:
<221> NAME/KEY: VARIANT
<222> LOCATION: 1
<223> OTHER INFORMATION: Xaa is Arg or Gly
<220> FEATURE:
<221> NAME/KEY: VARIANT
<222> LOCATION: 4
<223> OTHER INFORMATION: Xaa is Thr or Asn
<220> FEATURE:
<221> NAME/KEY: VARIANT
<222> LOCATION: 6
<223> OTHER INFORMATION: Xaa is Glu or Ala

<400> SEQUENCE: 87

Xaa Ala Ser Xaa Leu Xaa Ser
1               5

<210> SEQ ID NO 88
<211> LENGTH: 12
<212> TYPE: PRT
<213> ORGANISM: Oryctolagus cuniculus

```
<220> FEATURE:
<221> NAME/KEY: VARIANT
<222> LOCATION: 5
<223> OTHER INFORMATION: Xaa is Trp or Tyr
<220> FEATURE:
<221> NAME/KEY: VARIANT
<222> LOCATION: 6
<223> OTHER INFORMATION: Xaa is Gly or Ser
<220> FEATURE:
<221> NAME/KEY: VARIANT
<222> LOCATION: 7
<223> OTHER INFORMATION: Xaa is Ser or Asp
<220> FEATURE:
<221> NAME/KEY: VARIANT
<222> LOCATION: 8
<223> OTHER INFORMATION: Xaa is Thr, Ala, or Ser
<220> FEATURE:
<221> NAME/KEY: VARIANT
<222> LOCATION: 10
<223> OTHER INFORMATION: Xaa is Asp or Glu

<400> SEQUENCE: 88

Gln Gly Tyr Tyr Xaa Xaa Xaa Xaa Ala Xaa Asn Ala
1               5                   10

<210> SEQ ID NO 89
<211> LENGTH: 6
<212> TYPE: PRT
<213> ORGANISM: Oryctolagus cuniculus
<220> FEATURE:
<221> NAME/KEY: VARIANT
<222> LOCATION: 5
<223> OTHER INFORMATION: Xaa is Met or Ile

<400> SEQUENCE: 89

Ser Ser Tyr Asn Xaa Cys
1               5

<210> SEQ ID NO 90
<211> LENGTH: 18
<212> TYPE: PRT
<213> ORGANISM: Oryctolagus cuniculus
<220> FEATURE:
<221> NAME/KEY: VARIANT
<222> LOCATION: 6
<223> OTHER INFORMATION: Xaa is Asp or Ser

<400> SEQUENCE: 90

Cys Ile His Gly Gly Xaa Asp Gly Thr Thr Tyr Tyr Ala Thr Trp Ala
1               5                   10                  15

Lys Gly

<210> SEQ ID NO 91
<211> LENGTH: 10
<212> TYPE: PRT
<213> ORGANISM: Oryctolagus cuniculus
<220> FEATURE:
<221> NAME/KEY: VARIANT
<222> LOCATION: 9
<223> OTHER INFORMATION: Xaa is Lys or Asn

<400> SEQUENCE: 91

Asp Glu Trp Ala Gly Thr Arg Leu Xaa Leu
1               5                   10

<210> SEQ ID NO 92
<211> LENGTH: 11
<212> TYPE: PRT
<213> ORGANISM: Oryctolagus cuniculus
<220> FEATURE:
<221> NAME/KEY: VARIANT
```

```
<222> LOCATION: 5
<223> OTHER INFORMATION: Xaa is Thr or Ser
<220> FEATURE:
<221> NAME/KEY: VARIANT
<222> LOCATION: 8
<223> OTHER INFORMATION: Xaa is Thr or Ser
<220> FEATURE:
<221> NAME/KEY: VARIANT
<222> LOCATION: 9
<223> OTHER INFORMATION: Xaa is Phe or Trp

<400> SEQUENCE: 92

Gln Ala Ser Glu Xaa Ile Asn Xaa Xaa Leu Ser
1               5                   10

<210> SEQ ID NO 93
<211> LENGTH: 7
<212> TYPE: PRT
<213> ORGANISM: Oryctolagus cuniculus

<400> SEQUENCE: 93

Gln Ala Ser Thr Leu Ala Ser
1               5

<210> SEQ ID NO 94
<211> LENGTH: 13
<212> TYPE: PRT
<213> ORGANISM: Oryctolagus cuniculus
<220> FEATURE:
<221> NAME/KEY: VARIANT
<222> LOCATION: 6
<223> OTHER INFORMATION: Xaa is Gly or Lys
<220> FEATURE:
<221> NAME/KEY: VARIANT
<222> LOCATION: 9
<223> OTHER INFORMATION: Xaa is Asn or Ser
<220> FEATURE:
<221> NAME/KEY: VARIANT
<222> LOCATION: 13
<223> OTHER INFORMATION: Xaa is Val or Ile

<400> SEQUENCE: 94

Gln Ser Tyr Phe Tyr Xaa Ser Gly Xaa Tyr Gly Phe Xaa
1               5                   10

<210> SEQ ID NO 95
<211> LENGTH: 5
<212> TYPE: PRT
<213> ORGANISM: Oryctolagus cuniculus
<220> FEATURE:
<221> NAME/KEY: VARIANT
<222> LOCATION: 1
<223> OTHER INFORMATION: Xaa is Thr, Ser, Ile, or Val
<220> FEATURE:
<221> NAME/KEY: VARIANT
<222> LOCATION: 4
<223> OTHER INFORMATION: Xaa is Gly or Met
<220> FEATURE:
<221> NAME/KEY: VARIANT
<222> LOCATION: 5
<223> OTHER INFORMATION: Xaa is Ser or Asn

<400> SEQUENCE: 95

Xaa Tyr Glu Xaa Xaa
1               5

<210> SEQ ID NO 96
<211> LENGTH: 16
<212> TYPE: PRT
<213> ORGANISM: Oryctolagus cuniculus
<220> FEATURE:
<221> NAME/KEY: VARIANT
```

```
<222> LOCATION: 1
<223> OTHER INFORMATION: Xaa is Tyr or Val
<220> FEATURE:
<221> NAME/KEY: VARIANT
<222> LOCATION: 4
<223> OTHER INFORMATION: Xaa is Thr, Pro, or Ser
<220> FEATURE:
<221> NAME/KEY: VARIANT
<222> LOCATION: 6
<223> OTHER INFORMATION: Xaa is Ser or Gly
<220> FEATURE:
<221> NAME/KEY: VARIANT
<222> LOCATION: 7
<223> OTHER INFORMATION: Xaa is Asp or Ser
<220> FEATURE:
<221> NAME/KEY: VARIANT
<222> LOCATION: 12
<223> OTHER INFORMATION: Xaa is Thr or Ser

<400> SEQUENCE: 96

Xaa Ile Tyr Xaa Asp Xaa Xaa Thr Val Tyr Ala Xaa Trp Ala Lys Gly
1               5                   10                  15

<210> SEQ ID NO 97
<211> LENGTH: 11
<212> TYPE: PRT
<213> ORGANISM: Oryctolagus cuniculus
<220> FEATURE:
<221> NAME/KEY: VARIANT
<222> LOCATION: 1
<223> OTHER INFORMATION: Xaa is Gly or Thr
<220> FEATURE:
<221> NAME/KEY: VARIANT
<222> LOCATION: 4
<223> OTHER INFORMATION: Xaa is Ser or Asn
<220> FEATURE:
<221> NAME/KEY: VARIANT
<222> LOCATION: 5
<223> OTHER INFORMATION: Xaa is Ser or Thr
<220> FEATURE:
<221> NAME/KEY: VARIANT
<222> LOCATION: 10
<223> OTHER INFORMATION: Xaa is Ala, Asn, or Asp

<400> SEQUENCE: 97

Xaa Asp Leu Xaa Xaa Gly Trp Gly Ala Xaa Leu
1               5                   10

<210> SEQ ID NO 98
<211> LENGTH: 11
<212> TYPE: PRT
<213> ORGANISM: Oryctolagus cuniculus
<220> FEATURE:
<221> NAME/KEY: VARIANT
<222> LOCATION: 5
<223> OTHER INFORMATION: Xaa is Asn or Ser
<220> FEATURE:
<221> NAME/KEY: VARIANT
<222> LOCATION: 7
<223> OTHER INFORMATION: Xaa is Arg or Ser
<220> FEATURE:
<221> NAME/KEY: VARIANT
<222> LOCATION: 8
<223> OTHER INFORMATION: Xaa is Ser or Asn

<400> SEQUENCE: 98

Gln Ala Ser Glu Xaa Ile Xaa Xaa Trp Leu Ala
1               5                   10

<210> SEQ ID NO 99
<211> LENGTH: 7
<212> TYPE: PRT
<213> ORGANISM: Oryctolagus cuniculus
<220> FEATURE:
```

```
<221> NAME/KEY: VARIANT
<222> LOCATION: 4
<223> OTHER INFORMATION: Xaa is Lys, Ser, or Arg

<400> SEQUENCE: 99

Gln Ala Ser Xaa Leu Ala Ser
1               5

<210> SEQ ID NO 100
<211> LENGTH: 12
<212> TYPE: PRT
<213> ORGANISM: Oryctolagus cuniculus
<220> FEATURE:
<221> NAME/KEY: VARIANT
<222> LOCATION: 3
<223> OTHER INFORMATION: Xaa is Cys or Ser
<220> FEATURE:
<221> NAME/KEY: VARIANT
<222> LOCATION: 5
<223> OTHER INFORMATION: Xaa is Ser or Arg
<220> FEATURE:
<221> NAME/KEY: VARIANT
<222> LOCATION: 8
<223> OTHER INFORMATION: Xaa is Thr, Ala, Ser, or Ile
<220> FEATURE:
<221> NAME/KEY: VARIANT
<222> LOCATION: 11
<223> OTHER INFORMATION: Xaa is Ala or Gly

<400> SEQUENCE: 100

Gln Asn Xaa Tyr Xaa Phe Ser Xaa Tyr Gly Xaa Ala
1               5                   10

<210> SEQ ID NO 101
<211> LENGTH: 5
<212> TYPE: PRT
<213> ORGANISM: Oryctolagus cuniculus

<400> SEQUENCE: 101

Asn Tyr Tyr Trp Asn
1               5

<210> SEQ ID NO 102
<211> LENGTH: 16
<212> TYPE: PRT
<213> ORGANISM: Oryctolagus cuniculus

<400> SEQUENCE: 102

Phe Ile Asp Leu Leu Gly Ser Ala Asp Tyr Ala Ser Trp Ala Lys Gly
1               5                   10                  15

<210> SEQ ID NO 103
<211> LENGTH: 11
<212> TYPE: PRT
<213> ORGANISM: Oryctolagus cuniculus
<220> FEATURE:
<221> NAME/KEY: VARIANT
<222> LOCATION: 4
<223> OTHER INFORMATION: Xaa is His or Ser
<220> FEATURE:
<221> NAME/KEY: VARIANT
<222> LOCATION: 8
<223> OTHER INFORMATION: Xaa is Gly or Cys

<400> SEQUENCE: 103

Ser Gly Ser Xaa Ser Gly Trp Xaa Ala Asp Ile
1               5                   10

<210> SEQ ID NO 104
<211> LENGTH: 11
```

```
<212> TYPE: PRT
<213> ORGANISM: Oryctolagus cuniculus
<220> FEATURE:
<221> NAME/KEY: VARIANT
<222> LOCATION: 7
<223> OTHER INFORMATION: Xaa is Asn or Ser
<220> FEATURE:
<221> NAME/KEY: VARIANT
<222> LOCATION: 8
<223> OTHER INFORMATION: Xaa is Thr or Ser

<400> SEQUENCE: 104

Gln Ala Ser Gln Ser Ile Xaa Xaa Trp Leu Ser
1               5                   10

<210> SEQ ID NO 105
<211> LENGTH: 7
<212> TYPE: PRT
<213> ORGANISM: Oryctolagus cuniculus

<400> SEQUENCE: 105

Gln Ala Ser Lys Leu Ala Ser
1               5

<210> SEQ ID NO 106
<211> LENGTH: 12
<212> TYPE: PRT
<213> ORGANISM: Oryctolagus cuniculus

<400> SEQUENCE: 106

Gln Asn Asn Tyr Leu Met Ala Thr Tyr Gly Gly Pro
1               5                   10

<210> SEQ ID NO 107
<211> LENGTH: 5
<212> TYPE: PRT
<213> ORGANISM: Oryctolagus cuniculus

<400> SEQUENCE: 107

Ser Tyr Tyr Met Asn
1               5

<210> SEQ ID NO 108
<211> LENGTH: 16
<212> TYPE: PRT
<213> ORGANISM: Oryctolagus cuniculus
<220> FEATURE:
<221> NAME/KEY: VARIANT
<222> LOCATION: 5
<223> OTHER INFORMATION: Xaa is Ser or Gly

<400> SEQUENCE: 108

Phe Ile Asp Phe Xaa Ser Asp Ala Tyr Tyr Ala Asn Trp Ala Lys Gly
1               5                   10                  15

<210> SEQ ID NO 109
<211> LENGTH: 11
<212> TYPE: PRT
<213> ORGANISM: Oryctolagus cuniculus
<220> FEATURE:
<221> NAME/KEY: VARIANT
<222> LOCATION: 6
<223> OTHER INFORMATION: Xaa is Ala or Gly

<400> SEQUENCE: 109

Ser Gly Val Asp Ser Xaa Trp Gly Phe Asp Leu
1               5                   10
```

```
<210> SEQ ID NO 110
<211> LENGTH: 11
<212> TYPE: PRT
<213> ORGANISM: Oryctolagus cuniculus

<400> SEQUENCE: 110

Gln Ala Ser Gln Ser Ile Arg Ser Trp Leu Ala
1               5                   10

<210> SEQ ID NO 111
<211> LENGTH: 7
<212> TYPE: PRT
<213> ORGANISM: Oryctolagus cuniculus

<400> SEQUENCE: 111

Glu Ala Ser Lys Leu Ala Phe
1               5

<210> SEQ ID NO 112
<211> LENGTH: 12
<212> TYPE: PRT
<213> ORGANISM: Oryctolagus cuniculus
<220> FEATURE:
<221> NAME/KEY: VARIANT
<222> LOCATION: 3
<223> OTHER INFORMATION: Xaa is Ser or Asp

<400> SEQUENCE: 112

Gln Asn Xaa Tyr Gly Trp Thr Ser Tyr Gly Ala Thr
1               5                   10

<210> SEQ ID NO 113
<211> LENGTH: 5
<212> TYPE: PRT
<213> ORGANISM: Oryctolagus cuniculus
<220> FEATURE:
<221> NAME/KEY: VARIANT
<222> LOCATION: 4
<223> OTHER INFORMATION: Xaa is Met or Ile

<400> SEQUENCE: 113

Ser Tyr Asp Xaa Ile
1               5

<210> SEQ ID NO 114
<211> LENGTH: 17
<212> TYPE: PRT
<213> ORGANISM: Oryctolagus cuniculus
<220> FEATURE:
<221> NAME/KEY: VARIANT
<222> LOCATION: 4
<223> OTHER INFORMATION: Xaa is Ala or Thr
<220> FEATURE:
<221> NAME/KEY: VARIANT
<222> LOCATION: 5
<223> OTHER INFORMATION: Xaa is Val or Ile
<220> FEATURE:
<221> NAME/KEY: VARIANT
<222> LOCATION: 9
<223> OTHER INFORMATION: Xaa is Thr or Arg

<400> SEQUENCE: 114

Tyr Ile Asp Xaa Xaa Gly Ser Ser Xaa Tyr Tyr Ala Ser Trp Ala Lys
1               5                   10                  15

Gly

<210> SEQ ID NO 115
<211> LENGTH: 11
<212> TYPE: PRT
```

-continued

```
<213> ORGANISM: Oryctolagus cuniculus

<400> SEQUENCE: 115

Gly Asp Trp Ser Thr Ala Trp Gly Phe Asn Leu
1               5                   10

<210> SEQ ID NO 116
<211> LENGTH: 11
<212> TYPE: PRT
<213> ORGANISM: Oryctolagus cuniculus

<400> SEQUENCE: 116

Gln Ala Ser Gln Ser Ile Ser Gly Trp Leu Ser
1               5                   10

<210> SEQ ID NO 117
<211> LENGTH: 7
<212> TYPE: PRT
<213> ORGANISM: Oryctolagus cuniculus

<400> SEQUENCE: 117

Gln Ala Ser Lys Leu Ala Ser
1               5

<210> SEQ ID NO 118
<211> LENGTH: 12
<212> TYPE: PRT
<213> ORGANISM: Oryctolagus cuniculus
<220> FEATURE:
<221> NAME/KEY: VARIANT
<222> LOCATION: 6
<223> OTHER INFORMATION: Xaa is Ile or Val

<400> SEQUENCE: 118

Gln Ser Val Tyr Leu Xaa Ser Thr Tyr Gly Ala Thr
1               5                   10

<210> SEQ ID NO 119
<211> LENGTH: 5
<212> TYPE: PRT
<213> ORGANISM: Oryctolagus cuniculus
<220> FEATURE:
<221> NAME/KEY: VARIANT
<222> LOCATION: 4
<223> OTHER INFORMATION: Xaa is Val or Met

<400> SEQUENCE: 119

Ser Tyr Ala Xaa Ser
1               5

<210> SEQ ID NO 120
<211> LENGTH: 16
<212> TYPE: PRT
<213> ORGANISM: Oryctolagus cuniculus
<220> FEATURE:
<221> NAME/KEY: VARIANT
<222> LOCATION: 3
<223> OTHER INFORMATION: Xaa is Ser or Thr
<220> FEATURE:
<221> NAME/KEY: VARIANT
<222> LOCATION: 6
<223> OTHER INFORMATION: Xaa is Gly or Val
<220> FEATURE:
<221> NAME/KEY: VARIANT
<222> LOCATION: 7
<223> OTHER INFORMATION: Xaa is Ser or Ile

<400> SEQUENCE: 120

Ile Ile Xaa Ser Ser Xaa Xaa Thr Tyr Tyr Ala Ser Trp Ala Lys Gly
```

```
                          1               5                  10                 15
```

<210> SEQ ID NO 121
<211> LENGTH: 15
<212> TYPE: PRT
<213> ORGANISM: Oryctolagus cuniculus
<220> FEATURE:
<221> NAME/KEY: VARIANT
<222> LOCATION: 3
<223> OTHER INFORMATION: Xaa is Asn or Ser
<220> FEATURE:
<221> NAME/KEY: VARIANT
<222> LOCATION: 5
<223> OTHER INFORMATION: Xaa is Arg or Thr

<400> SEQUENCE: 121

```
Asp Ala Xaa Ser Xaa Gly Tyr Tyr Ile Pro Tyr Tyr Phe Asn Ile
1               5                   10                  15
```

<210> SEQ ID NO 122
<211> LENGTH: 11
<212> TYPE: PRT
<213> ORGANISM: Oryctolagus cuniculus

<400> SEQUENCE: 122

```
Gln Ala Ser Glu Ser Ile Tyr Ser Asn Leu Ala
1               5                   10
```

<210> SEQ ID NO 123
<211> LENGTH: 7
<212> TYPE: PRT
<213> ORGANISM: Oryctolagus cuniculus
<220> FEATURE:
<221> NAME/KEY: VARIANT
<222> LOCATION: 3
<223> OTHER INFORMATION: Xaa is Ser or Phe

<400> SEQUENCE: 123

```
Ala Ala Xaa Tyr Leu Ala Ser
1               5
```

<210> SEQ ID NO 124
<211> LENGTH: 12
<212> TYPE: PRT
<213> ORGANISM: Oryctolagus cuniculus
<220> FEATURE:
<221> NAME/KEY: VARIANT
<222> LOCATION: 4
<223> OTHER INFORMATION: Xaa is His or Asn

<400> SEQUENCE: 124

```
Gln Ser Ala Xaa Tyr Ser Ser Ser Gly Asp Ile Ala
1               5                   10
```

<210> SEQ ID NO 125
<211> LENGTH: 5
<212> TYPE: PRT
<213> ORGANISM: Oryctolagus cuniculus

<400> SEQUENCE: 125

```
Ser Tyr Ala Met Gly
1               5
```

<210> SEQ ID NO 126
<211> LENGTH: 17
<212> TYPE: PRT
<213> ORGANISM: Oryctolagus cuniculus

<400> SEQUENCE: 126

Ile Ile Tyr Leu Glu Thr Gly Asn Thr Tyr Tyr Ala Thr Trp Ala Lys
1               5                   10                  15

Gly

<210> SEQ ID NO 127
<211> LENGTH: 8
<212> TYPE: PRT
<213> ORGANISM: Oryctolagus cuniculus

<400> SEQUENCE: 127

Gly Ser Trp Ser Asp Tyr Ala Leu
1               5

<210> SEQ ID NO 128
<211> LENGTH: 13
<212> TYPE: PRT
<213> ORGANISM: Oryctolagus cuniculus

<400> SEQUENCE: 128

Gln Ser Ser Gln Asn Val Tyr Ser Asn Asp Leu Leu Ser
1               5                   10

<210> SEQ ID NO 129
<211> LENGTH: 7
<212> TYPE: PRT
<213> ORGANISM: Oryctolagus cuniculus

<400> SEQUENCE: 129

Glu Ala Ser Lys Leu Ala Ser
1               5

<210> SEQ ID NO 130
<211> LENGTH: 10
<212> TYPE: PRT
<213> ORGANISM: Oryctolagus cuniculus

<400> SEQUENCE: 130

Ala Gly Ala Tyr Ser Gly Asn Ile Asn Val
1               5                   10

<210> SEQ ID NO 131
<211> LENGTH: 18
<212> TYPE: PRT
<213> ORGANISM: Oryctolagus cuniculus
<220> FEATURE:
<221> NAME/KEY: VARIANT
<222> LOCATION: 1
<223> OTHER INFORMATION: Xaa is Cys, Phe, Tyr, or Ile
<220> FEATURE:
<221> NAME/KEY: VARIANT
<222> LOCATION: 3
<223> OTHER INFORMATION: Xaa is Met, Tyr, Asp, or Ser
<220> FEATURE:
<221> NAME/KEY: VARIANT
<222> LOCATION: 4
<223> OTHER INFORMATION: Xaa is Thr or no residue
<220> FEATURE:
<221> NAME/KEY: VARIANT
<222> LOCATION: 5
<223> OTHER INFORMATION: Xaa is Gly or no residue
<220> FEATURE:
<221> NAME/KEY: NON_CONS
<222> LOCATION: (6)...(9)
<223> OTHER INFORMATION: Xaa is any amino acid
<220> FEATURE:
<221> NAME/KEY: VARIANT
<222> LOCATION: 10
<223> OTHER INFORMATION: Xaa is Thr or Ala
<220> FEATURE:

```
<221> NAME/KEY: VARIANT
<222> LOCATION: (11)...(11)
<223> OTHER INFORMATION: Xaa is Try, Glu, Asp, or Val
<220> FEATURE:
<221> NAME/KEY: VARIANT
<222> LOCATION: (14)...(14)
<223> OTHER INFORMATION: Xaa is Asn, Ser, or Thr
<220> FEATURE:
<221> NAME/KEY: VARIANT
<222> LOCATION: (18)...(18)
<223> OTHER INFORMATION: Xaa is Gly or Ser

<400> SEQUENCE: 131

Xaa Ile Xaa Xaa Xaa Xaa Xaa Xaa Xaa Xaa Xaa Tyr Ala Xaa Trp Ala
1               5                   10                  15

Lys Xaa

<210> SEQ ID NO 132
<211> LENGTH: 7
<212> TYPE: PRT
<213> ORGANISM: Oryctolagus cuniculus
<220> FEATURE:
<221> NAME/KEY: NON_CONS
<222> LOCATION: 1
<223> OTHER INFORMATION: Xaa is any amino acid
<220> FEATURE:
<221> NAME/KEY: VARIANT
<222> LOCATION: 4
<223> OTHER INFORMATION: Xaa is Thr, Lys, or Tyr
<220> FEATURE:
<221> NAME/KEY: VARIANT
<222> LOCATION: 6
<223> OTHER INFORMATION: Xaa is Ala or Glu

<400> SEQUENCE: 132

Xaa Ala Ser Xaa Leu Xaa Ser
1               5
```